United States Patent
Karasawa et al.

(10) Patent No.: US 8,317,814 B2
(45) Date of Patent: Nov. 27, 2012

(54) MEDICAL DEVICE AND PROCESS OF INSTALLING MEDICAL DEVICE IN PATIENT

(75) Inventors: Hitoshi Karasawa, Hachioji (JP); Sho Nakajima, Hachioji (JP); Daisuke Asada, Hachioji (JP); Keiji Handa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 685 days.

(21) Appl. No.: 12/349,844

(22) Filed: Jan. 7, 2009

(65) Prior Publication Data

US 2009/0187073 A1 Jul. 23, 2009

(30) Foreign Application Priority Data

Jan. 22, 2008 (JP) ................................. 2008-011820

(51) Int. Cl.
*A61B 17/34* (2006.01)
(52) U.S. Cl. ..................................... 606/185
(58) Field of Classification Search ............... 606/185, 606/129, 130, 232; 600/202–208, 114–115; 604/164.01, 288.01, 288.04
See application file for complete search history.

(56) References Cited

U.S. PATENT DOCUMENTS

| | | | |
|---|---|---|---|
| 5,167,627 A | 12/1992 | Clegg et al. | |
| 5,342,382 A * | 8/1994 | Brinkerhoff et al. | 606/184 |
| 5,813,976 A | 9/1998 | Filipi et al. | |
| 6,081,738 A * | 6/2000 | Hinohara et al. | 600/407 |
| 6,110,183 A | 8/2000 | Cope | |
| 2002/0165589 A1 * | 11/2002 | Imran et al. | 607/40 |
| 2005/0165449 A1 | 7/2005 | Cadeddu et al. | |
| 2006/0058575 A1 | 3/2006 | Zaddem et al. | |
| 2006/0074307 A1 | 4/2006 | Igarashi et al. | |
| 2007/0073102 A1 | 3/2007 | Matsuno et al. | |
| 2007/0161855 A1 | 7/2007 | Mikkaichi et al. | |

FOREIGN PATENT DOCUMENTS

| | | |
|---|---|---|
| EP | 1 769 714 A1 | 4/2007 |
| JP | 2005-237979 | 9/2005 |
| JP | 2007-260397 A | 10/2007 |

* cited by examiner

*Primary Examiner* — Ryan Severson
*Assistant Examiner* — Anh Dang
(74) *Attorney, Agent, or Firm* — Scully, Scott, Murphy & Presser, PC

(57) ABSTRACT

A medical device includes: a medical instrument introduced into a body cavity and having a contact portion that is fixed in contact with a wall within a body, and a wire; an extracorporeal device installed on a body surface and having a hole portion through which the wire can be inserted and removed, fixing mechanisms for fixing the wire inserted through the hole portion, and a housing that is fixed in contact with the body surface; and a pressure adjusting portion provided in one of the medical instrument and the extracorporeal device for maintaining a predetermined tensile force or more that is applied to the wire when the wire is fixed by the fixing mechanism with a body wall being sandwiched between the contact portion and the housing.

9 Claims, 18 Drawing Sheets

MEDICAL DEVICE AND PROCESS OF INSTALLING MEDICAL DEVICE IN PATIENT

This application claims benefit of Japanese Application No. 2008-011820 filed in Japan on Jan. 22, 2008, the contents of which are incorporated by this reference.

BACKGROUND OF THE INVENTION

1. Field of the Invention

The present invention relates to a medical device including a medical instrument fixed to an inner side of an abdominal cavity wall and a process of installing a medical device in a patient.

2. Description of the Related Art

As is generally known, an endoscope, which is a medical instrument, includes an image pickup apparatus, and is introduced into a body cavity of a patient to perform various examinations and treatments of a diseased part within a body with an observation image shot by the image pickup apparatus.

Such an endoscope includes an endoscope that is introduced into digestive organs such as esophagus, stomach, large intestine and duodenum, which are a luminal path within a body, from an anus or oral cavity, and an endoscope that is introduced into an abdominal cavity from the vicinity of a navel by puncturing and penetrating a body wall. In general, the endoscope has a long insertion portion, which is inserted into a digestive path or an abdominal cavity.

In order to reduce patient pain caused by introducing the insertion portion, a capsule-type medical device as described in Japanese Patent Application Laid-Open Publication No. 2005-237979 has been recently proposed, for example. Japanese Patent Application Laid-Open Publication No. 2005-237979 discloses a capsule-type endoscope device technique which enables guiding to a target position through a tubular cavity while rotating upon reception of a rotating magnetic field from outside a body.

SUMMARY OF THE INVENTION

A medical device according to the present invention includes: a medical instrument introduced into a body cavity and having a contact portion that is fixed in contact with a wall within a body, and a wire; an extracorporeal device installed on a body surface and having a hole portion through which the wire can be inserted and removed, a fixing mechanism for fixing the wire inserted through the hole portion, and a housing that is fixed in contact with the body surface; and a pressure adjusting portion provided in one of the medical instrument and the extracorporeal device for maintaining a predetermined tensile force or more that is applied to the wire when the wire is fixed by the fixing mechanism with a body wall being sandwiched between the contact portion and the housing.

A process of installing a medical device in a patient according to the present invention is a process of installing a medical device in a patient, the medical device including: a medical instrument introduced into a body cavity and having a suction cup portion that is fixed to a wall within a body, and a wire extending from a center of a suction surface of the suction cup; an extracorporeal device installed on a body surface and having a puncture needle from and into which a hook portion for hooking the wire projects and retracts, and a hole portion through which the puncture needle can be inserted and removed; and a fixing portion provided in a housing of the extracorporeal device and fixing the wire that is inserted through the hole portion for maintaining a suction state of the suction cup portion to the wall within a body by maintaining a state in which a body wall is sandwiched between the medical instrument and the housing, and the process of installing the medical device includes: introducing the medical instrument into the abdominal cavity through a trocar by use of a treatment instrument; puncturing a predetermined position of an abdomen with the puncture needle from a body surface into the abdominal cavity; pulling the hook portion up to the body surface side of the abdomen with the wire connected to the medical instrument being hooked into the hook portion; removing the puncture needle from the extracorporeal device such that the wire is inserted through the extracorporeal device; placing the housing on the abdomen body surface along the wire while pulling the wire with a predetermined tensile force or more until the body wall is sandwiched between the medical instrument and the housing and the suction cup portion sticks to the wall within a body; and fixing the wire to the housing by the fixing portion.

The above and other objects, features and advantages of the invention will become more clearly understood from the following description referring to the accompanying drawings.

DETAILED DESCRIPTION OF THE PREFERRED EMBODIMENTS

In the following, embodiments of the present invention will be described with reference to the drawings. In the following description, a medical device for performing a laparoscopic surgery will be described as an example.

(First Embodiment)

Figure 1:
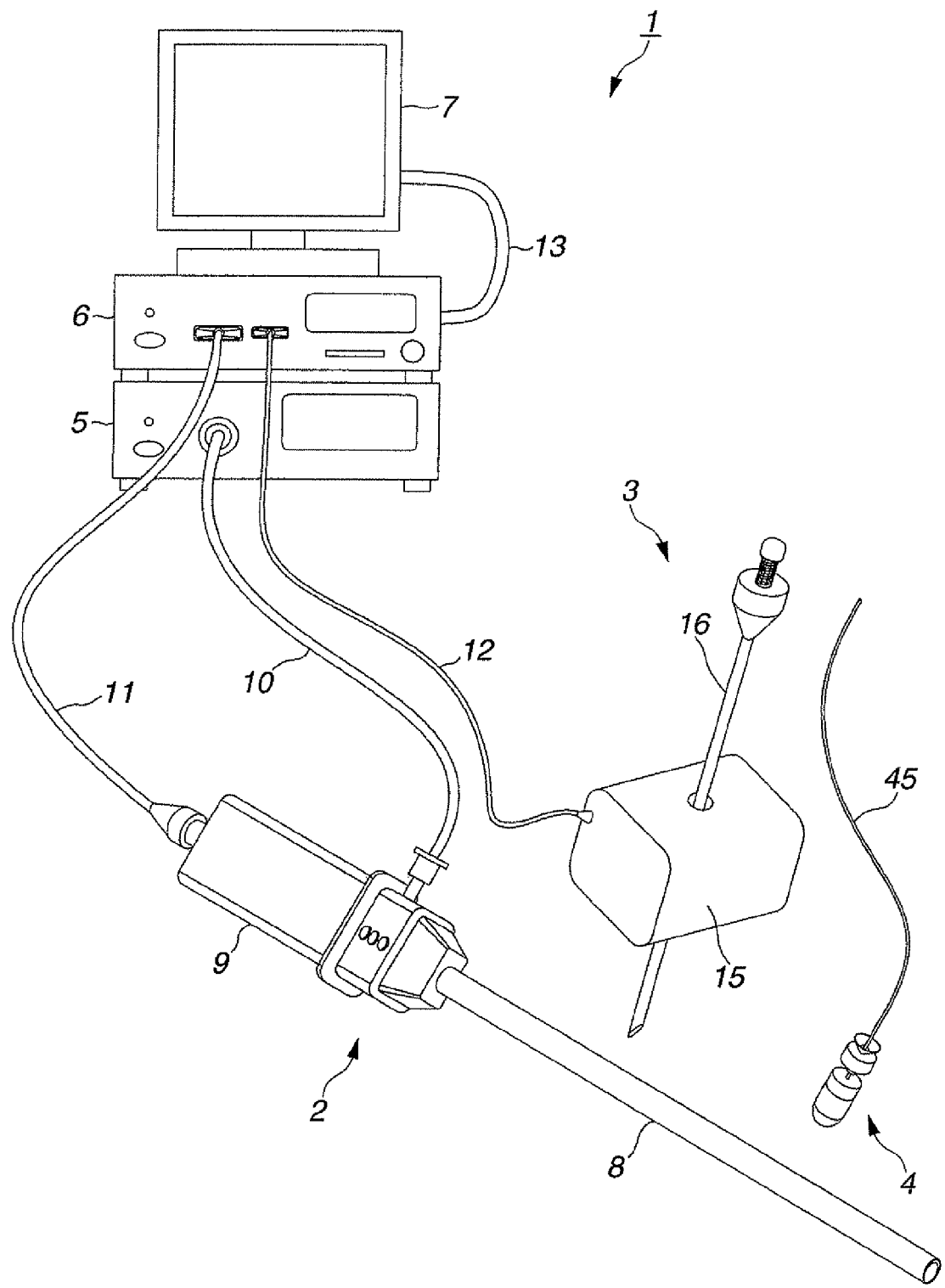
FIG. 1 is a view illustrating a configuration of an endoscope system that is a medical device according to a first embodiment of the present invention.
Figure 2:
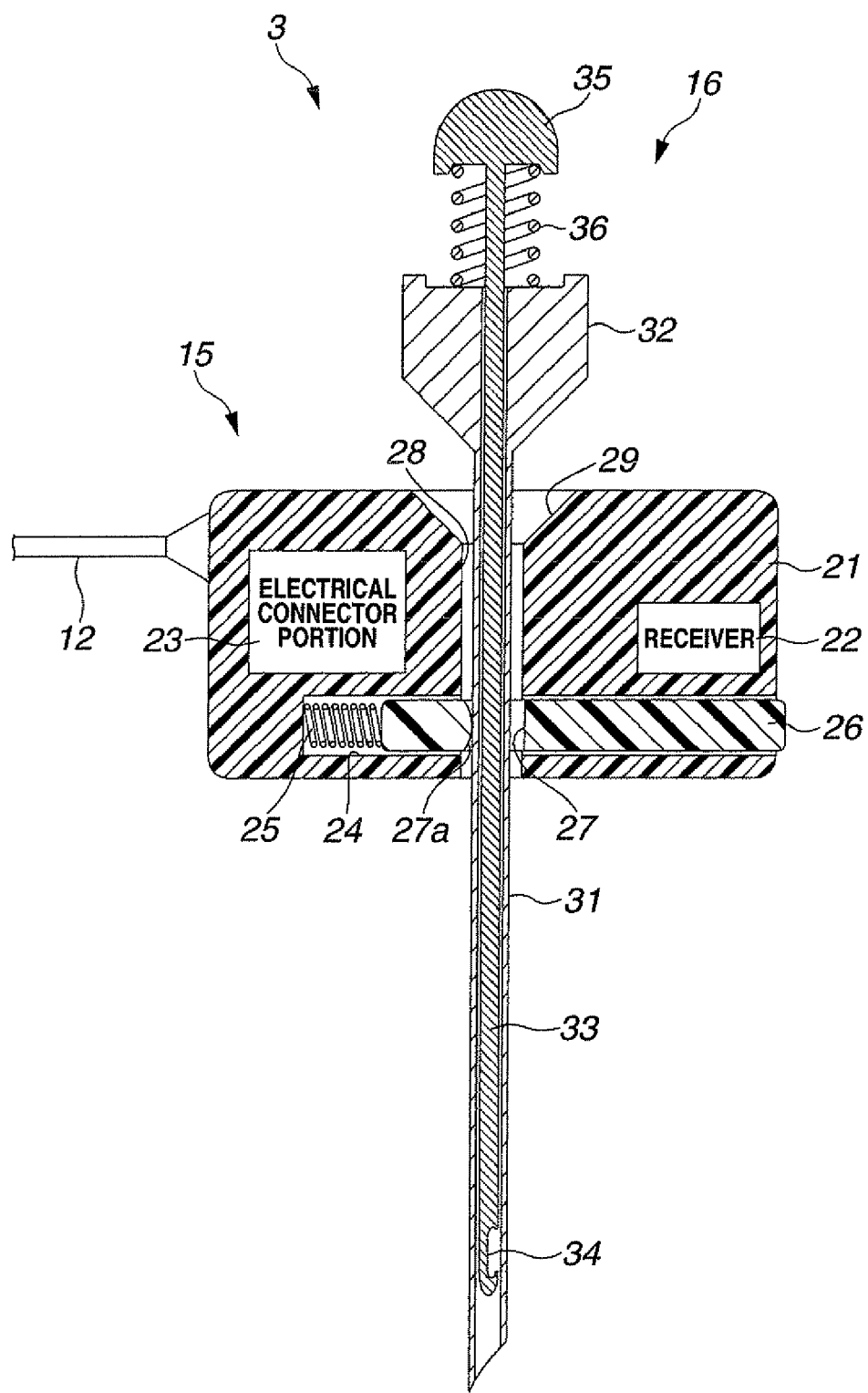
FIG. 2 is a sectional view illustrating a configuration of an extracorporeal device according to the first embodiment.
Figure 3:
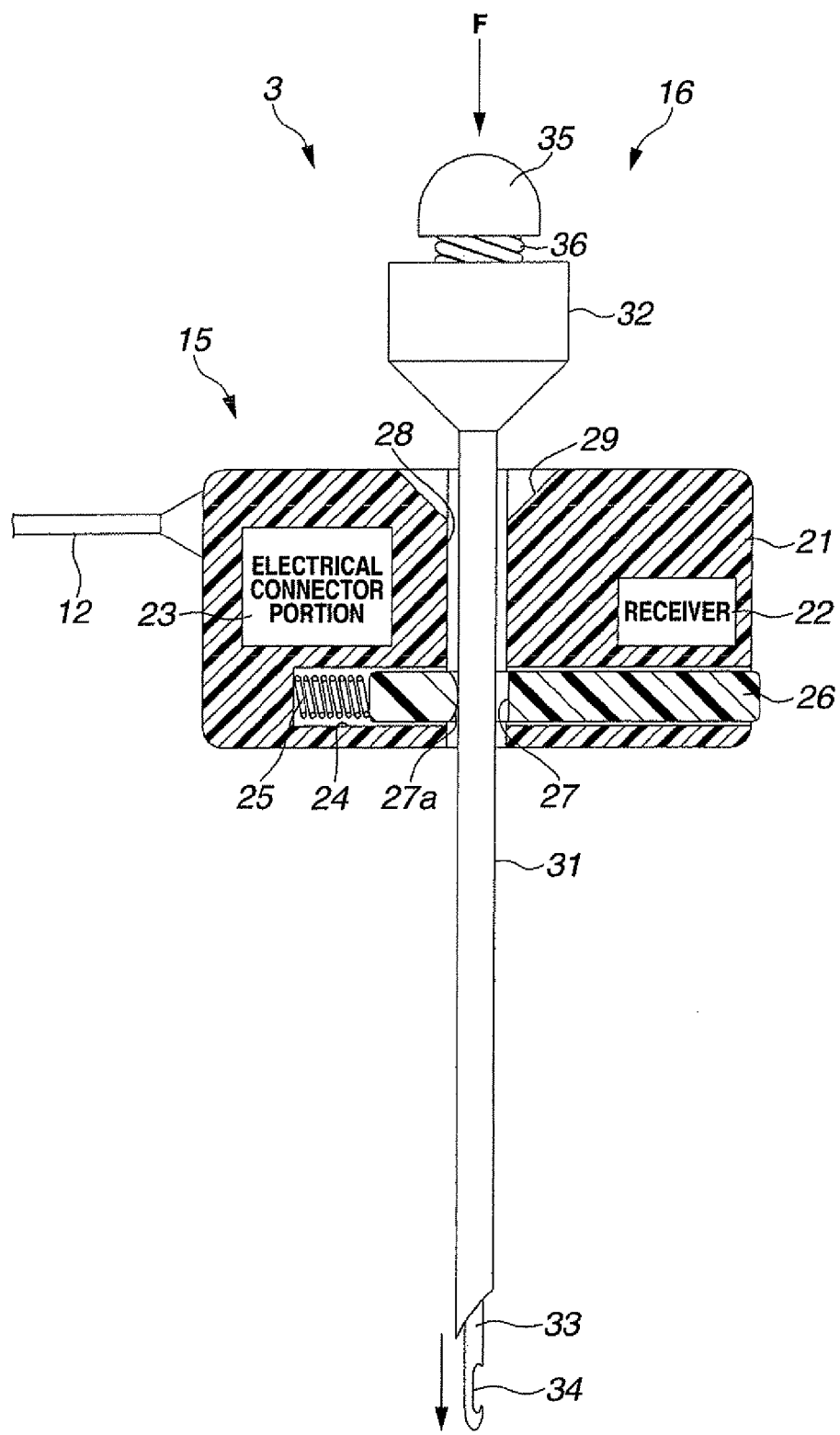
FIG. 3 is a top view illustrating an action of a puncture needle of an extracorporeal device according to the first embodiment.
Figure 4:
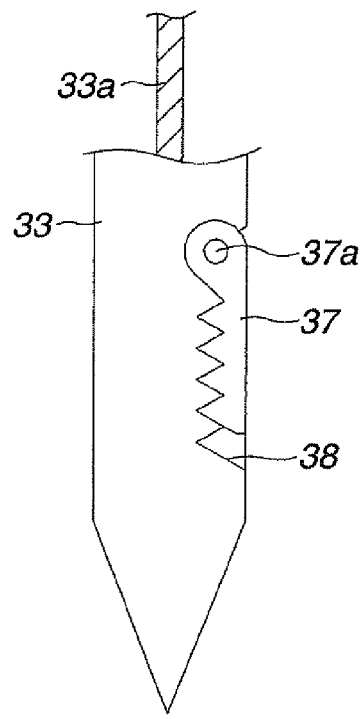
FIG. 4 is a view illustrating a puncture rod of a forceps-type puncture needle that is a first modification according to the first embodiment.
Figure 5:
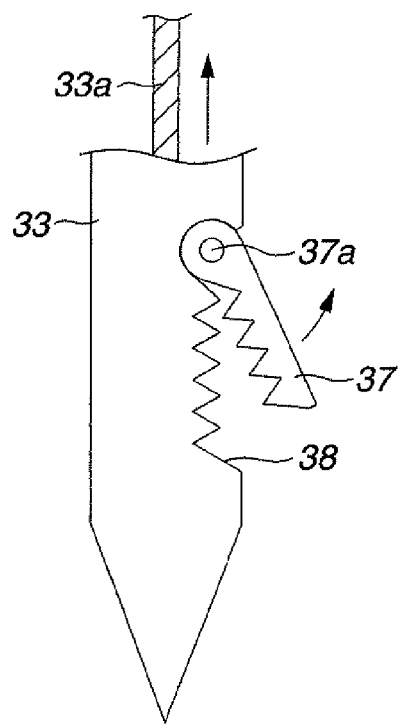
FIG. 5 is a view for explaining an operation of an opening and closing jaw of the forceps-type puncture needle in FIG. 4 according to the first embodiment.
Figure 6:
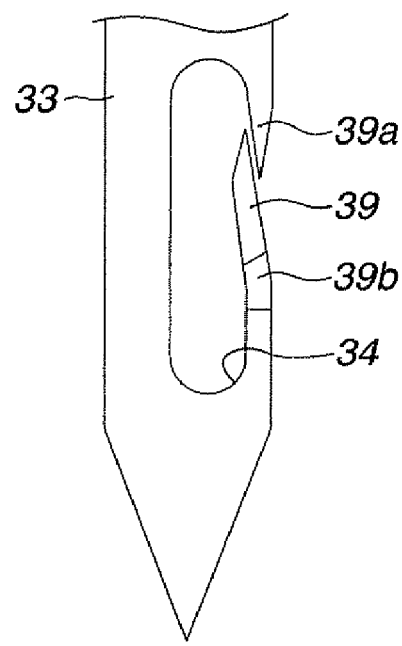
FIG. 6 is a view illustrating a puncture rod of a clip-type puncture needle that is a second modification according to the first embodiment.
Figure 7:
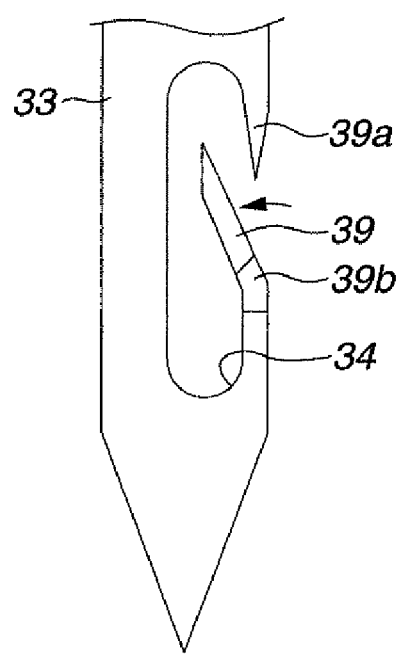
FIG. 7 is a view for explaining an operation of a claw portion of the clip-type puncture needle in FIG. 6 according to the first embodiment.
Figure 8:
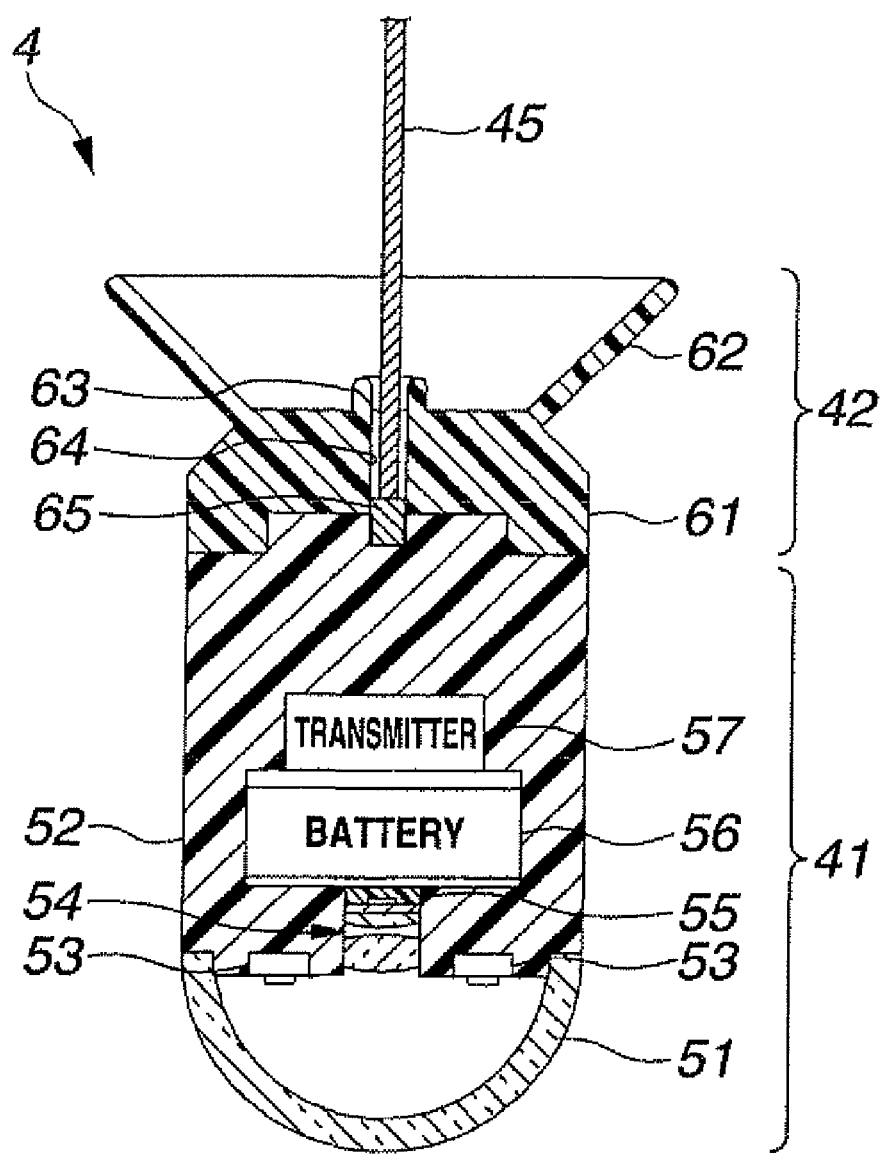
FIG. 8 is a sectional view illustrating a configuration of a camera to be installed in an abdominal cavity according to the first embodiment.
Figure 9:
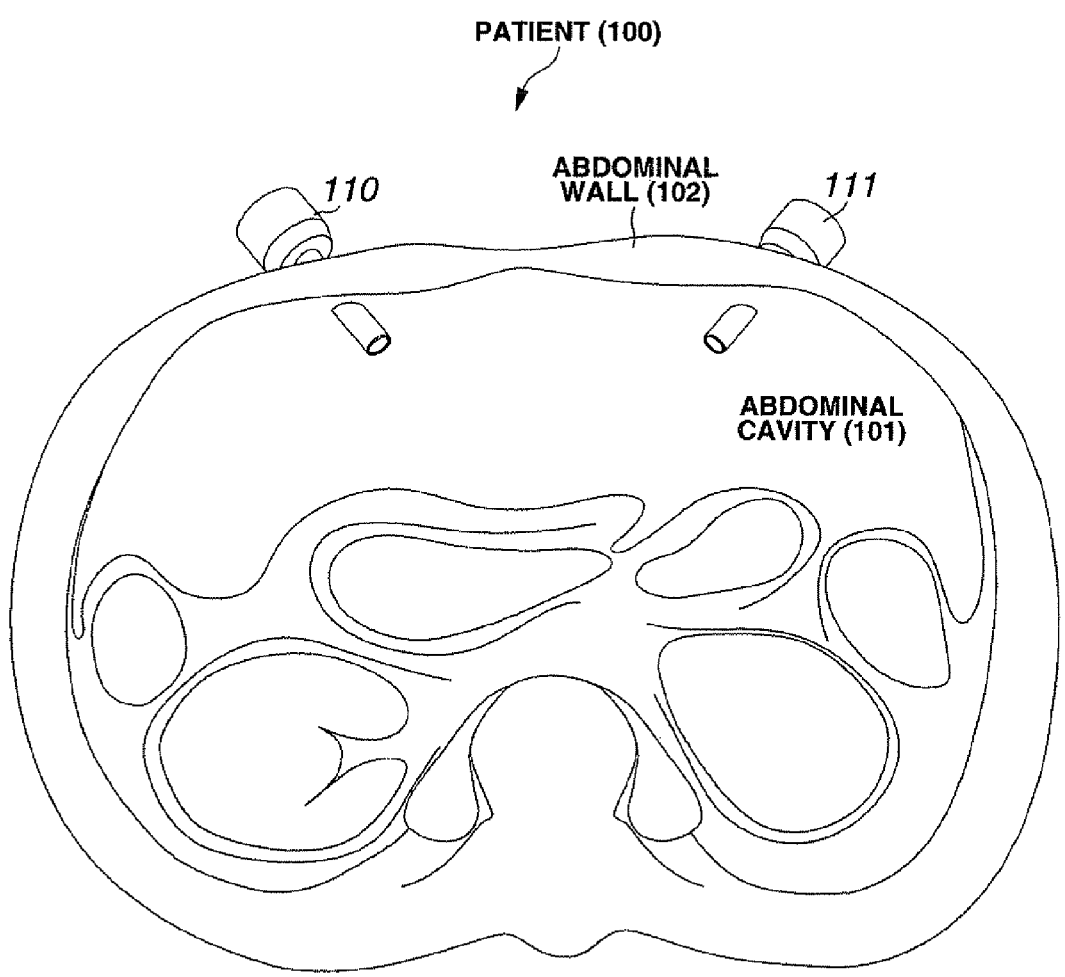
FIG. 9 is a view illustrating a state in which an abdominal wall of a patient is punctured with trocars according to the first embodiment.
Figure 10:
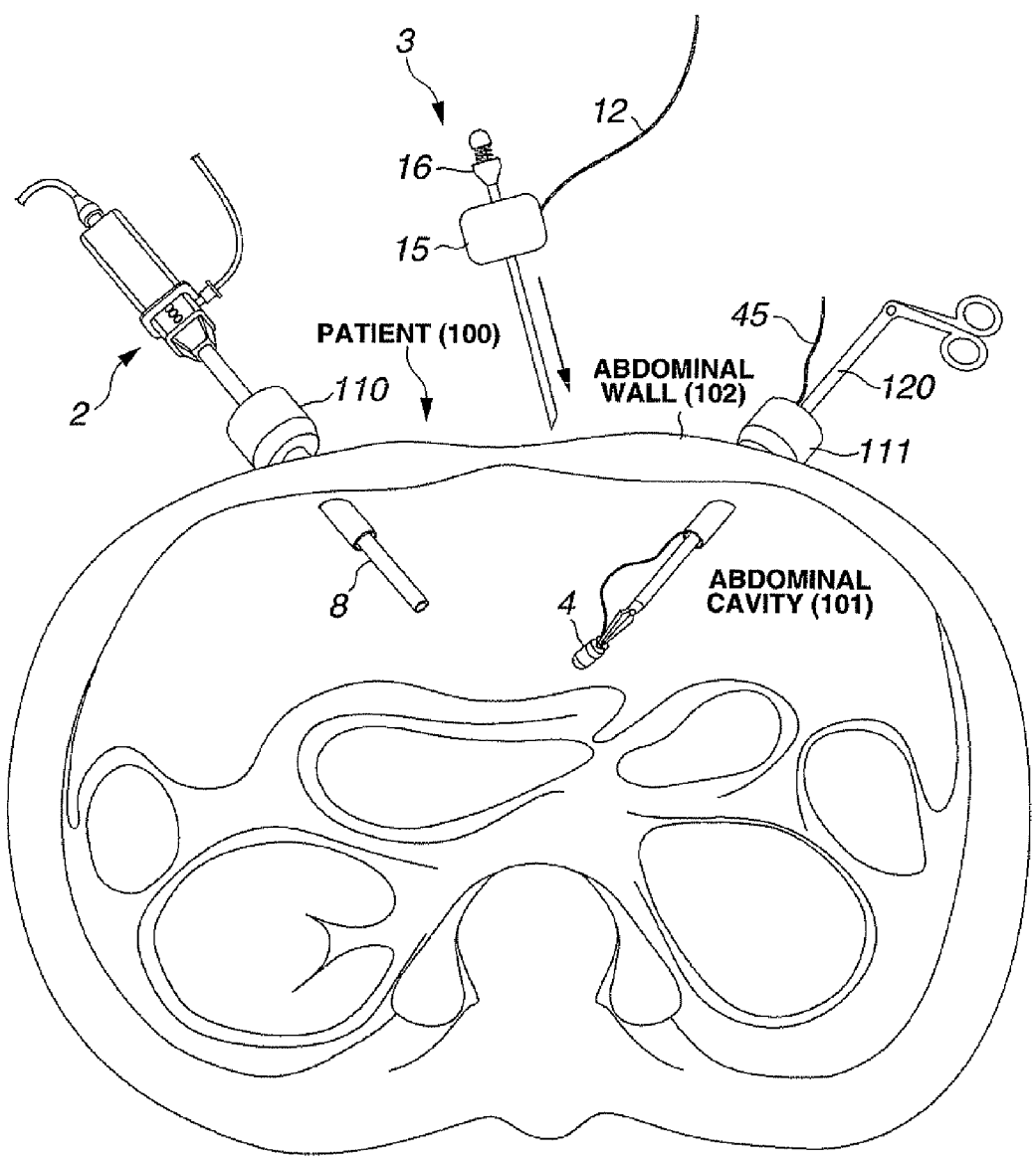
FIG. 10 is a view for explaining procedures for introducing a camera to be installed in an abdominal cavity into an abdominal cavity according to the first embodiment.
Figure 11:
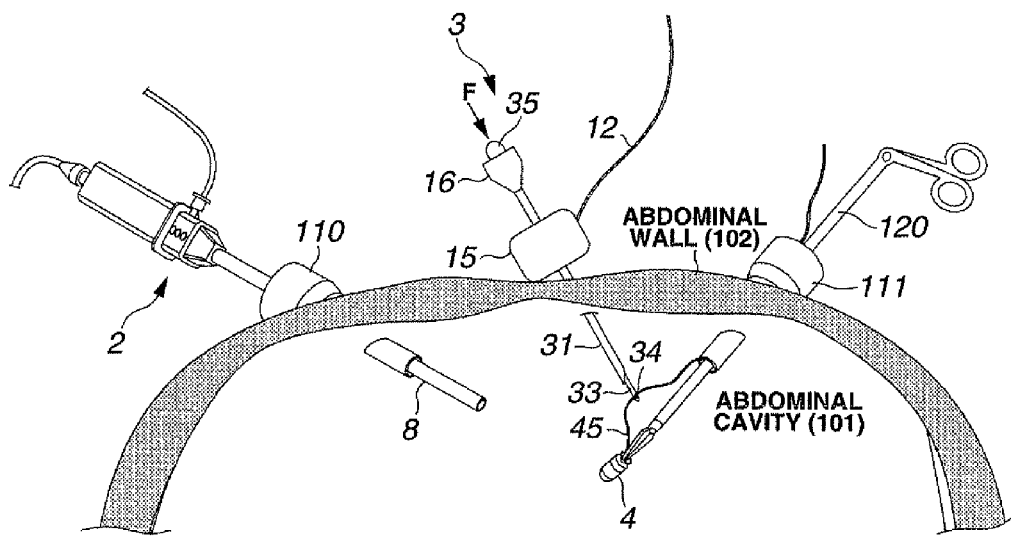
FIG. 11 is a view for explaining procedures for introducing a camera to be installed in an abdominal cavity into an abdominal cavity by illustrating a state in which an abdominal wall is punctured with a puncture needle to hook a wire of the camera to be installed in an abdominal cavity according to the first embodiment.
Figure 12:
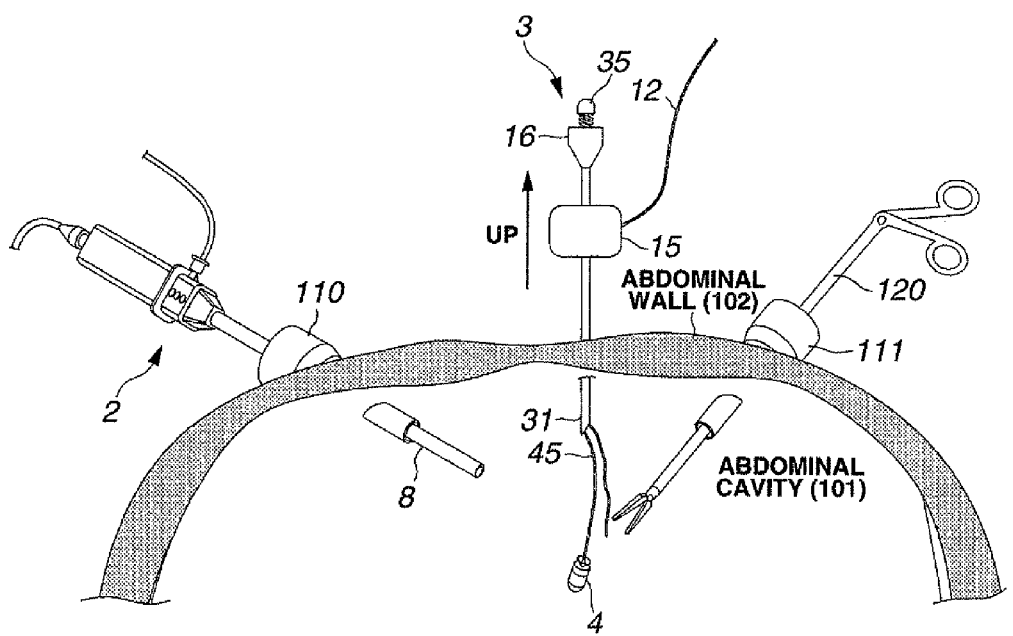
FIG. 12 is a view for explaining procedures for fixing a camera to be installed in an abdominal cavity to an abdominal wall by illustrating a state in which a puncture needle, which hooks a wire of the camera to be installed in an abdominal cavity, is pulled up according to the first embodiment.
Figure 13:
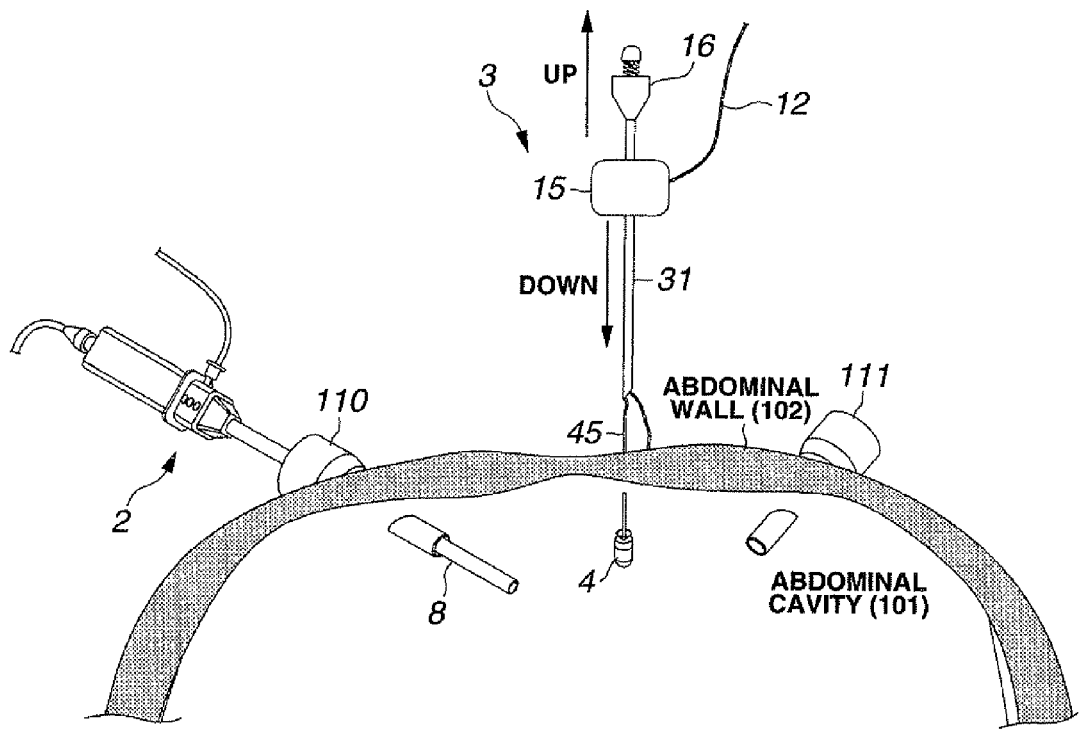
FIG. 13 is a view for explaining procedures for fixing a camera to be installed in an abdominal cavity to an abdominal wall by illustrating a state in which a puncture needle is pulled up and a fixing unit is lowered along the puncture needle according to the first embodiment.
Figure 14:
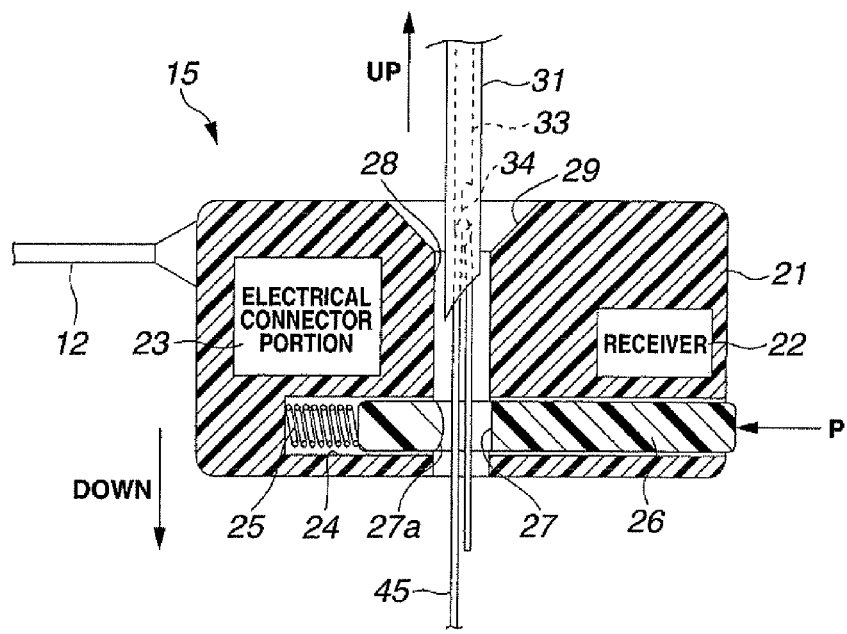
FIG. 14 is a sectional view for explaining an action of an extracorporeal device according to the first embodiment.
Figure 15:
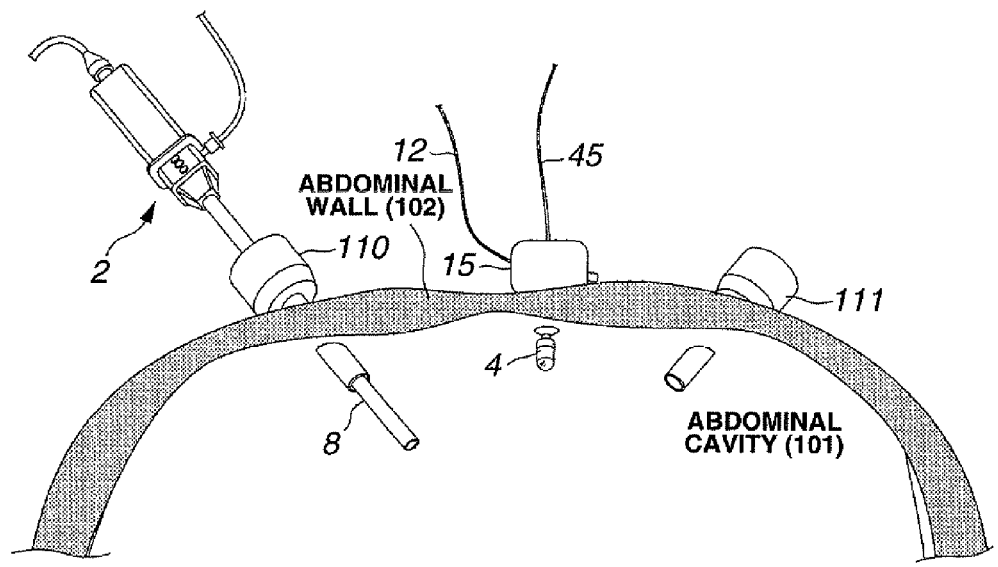
FIG. 15 is a view illustrating a state in which a fixing unit is installed on an abdomen and a camera to be installed in an abdominal cavity is fixed to an abdominal wall according to the first embodiment.
Figure 16:
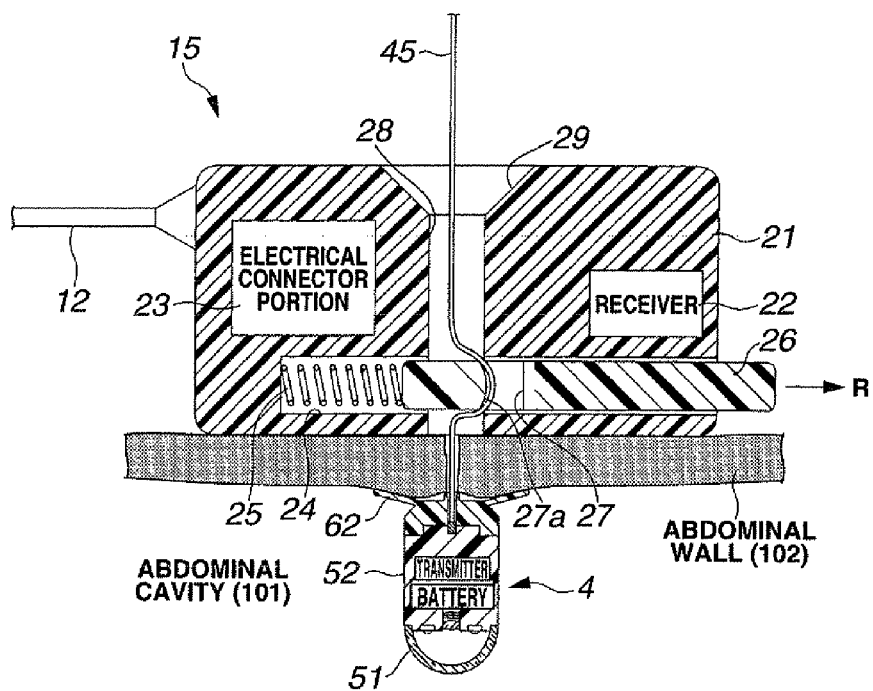
FIG. 16 is a sectional view of the fixing unit and the camera to be installed in an abdominal cavity in the state shown in FIG. 15 according to the first embodiment.
Figure 17:
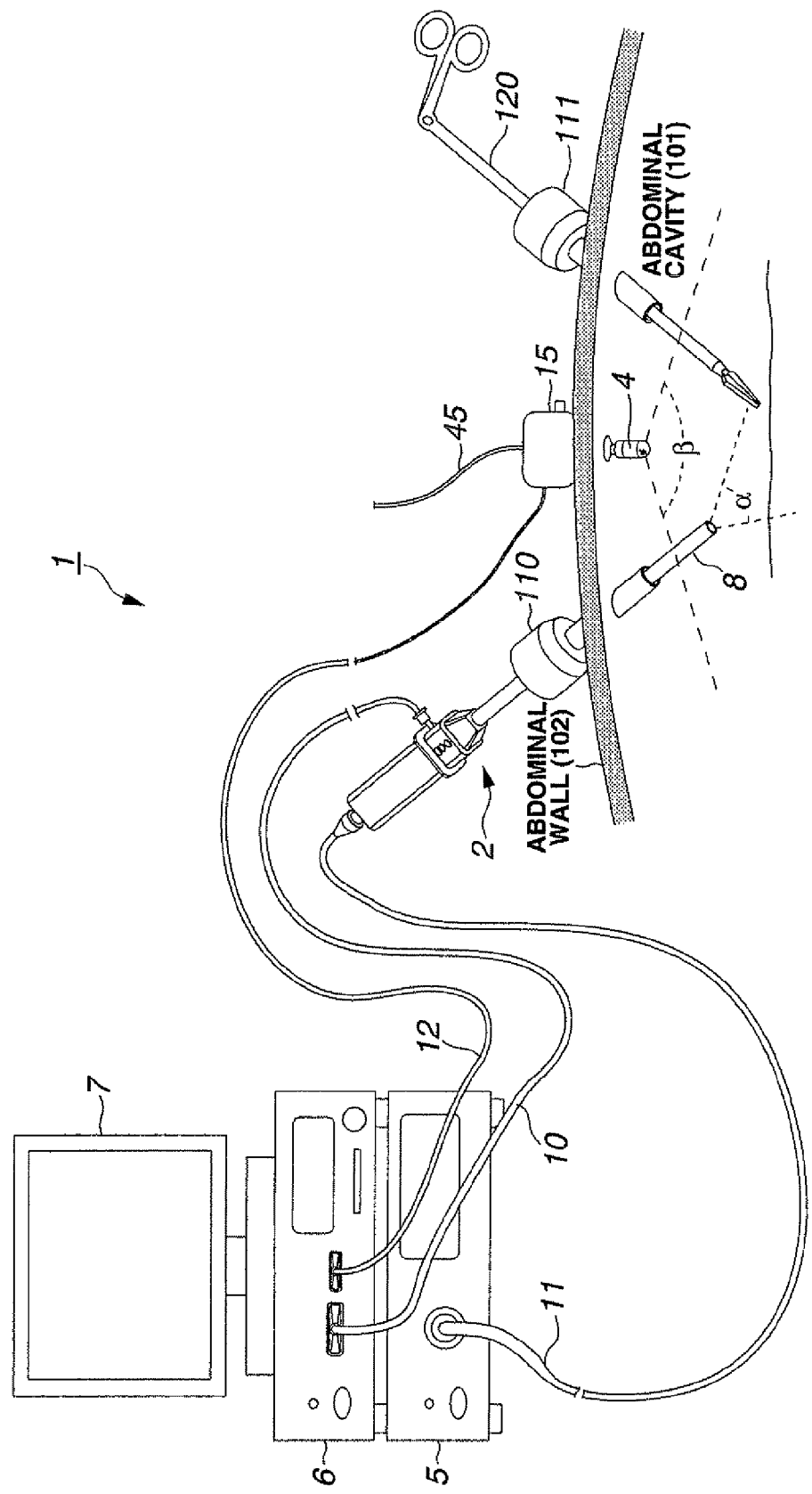
FIG. 17 is an entire configuration diagram of an endoscope system illustrating a state in which a camera to be installed in an abdominal cavity is fixed to an abdominal wall according to the first embodiment.
Figure 18:
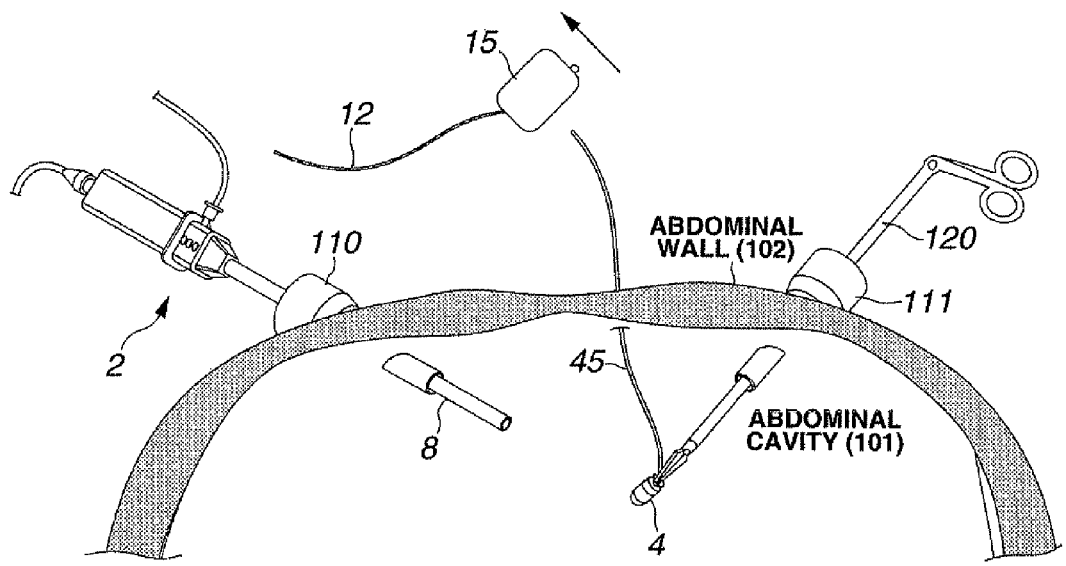
FIG. 18 is a sectional view for explaining procedures for removing a fixing unit from a wire of a camera to be installed in an abdominal cavity according to the first embodiment.
Figure 19:
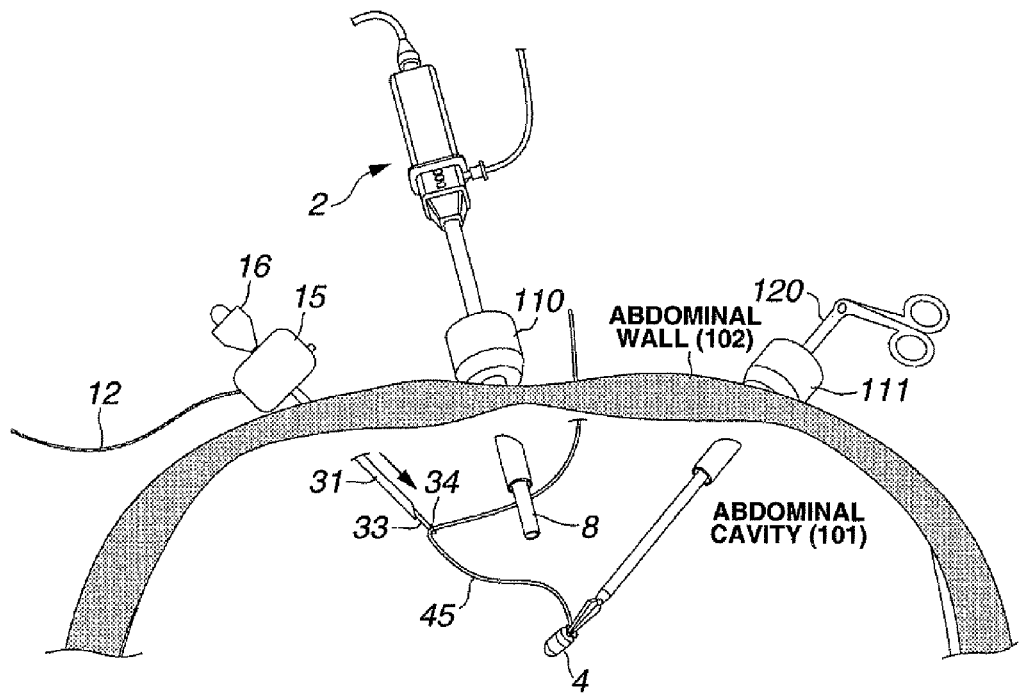
FIG. 19 is a view for explaining procedures for changing a position of a camera to be installed in an abdominal cavity by illustrating a state in which another position of an abdominal wall is punctured with a puncture needle to hook a wire of the camera to be installed in an abdominal cavity according to the first embodiment.
Figure 20:
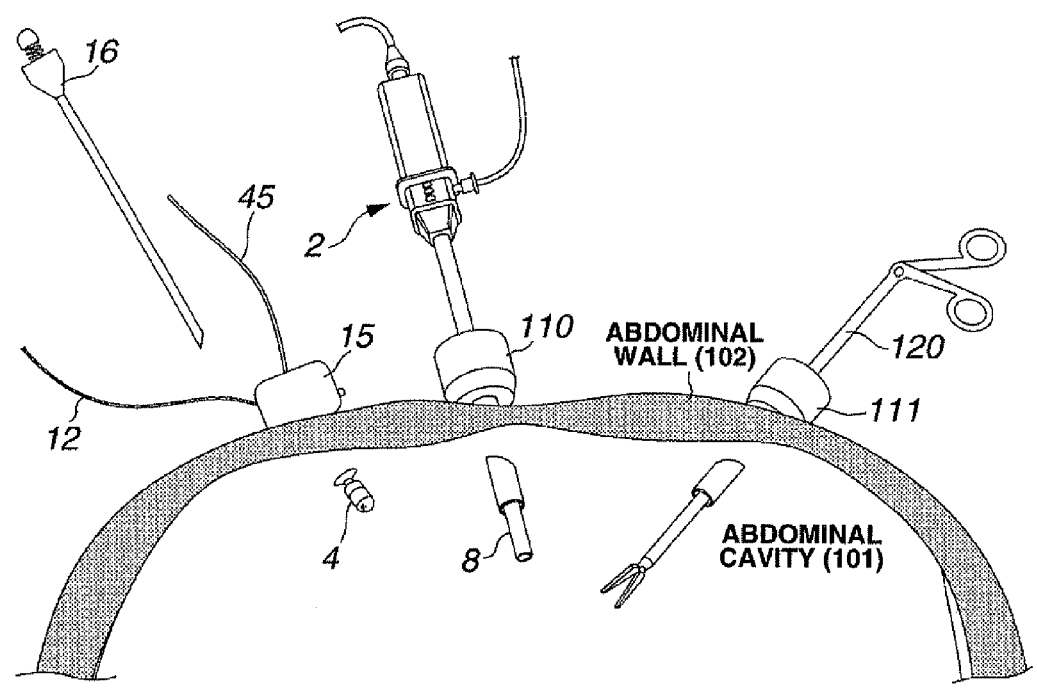
FIG. 20 is a view illustrating a state in which a fixing unit is installed on an abdomen and a camera to be installed in an abdominal cavity is fixed to an abdominal wall after changing the position according to the first embodiment.

First, an endoscope system that is a medical device according to the present invention used for a laparoscopic surgery will be described below. FIGS. 1 to 20 are related to a first embodiment of the present invention. FIG. 1 is a view illustrating a configuration of an endoscope system that is a medical device. FIG. 2 is a sectional view illustrating a configuration of an extracorporeal device. FIG. 3 is a top view illustrating an action of a hook needle of an extracorporeal device. FIG. 4 is a view illustrating a puncture rod of a forceps-type puncture needle that is a first modification. FIG. 5 is a view for explaining an operation of an opening and closing jaw of the forceps-type puncture needle in FIG. 4. FIG. 6 is a view illustrating a puncture rod of a clip-type puncture needle that is a second modification. FIG. 7 is a view for explaining an operation of a claw portion of the clip-type puncture needle in FIG. 6. FIG. 8 is a sectional view illustrating a configuration of a camera to be installed in an abdominal cavity. FIG. 9 is a view illustrating a state in which an abdominal wall of a patient is punctured with trocars. FIG. 10 is a view for explaining procedures for introducing a camera to be installed in an abdominal cavity into an abdominal cavity. FIG. 11 is a view for explaining procedures for introducing a camera to be installed in an abdominal cavity into an abdominal cavity by illustrating a state in which an abdominal wall is punctured with a hook needle to hook a wire of the camera to be installed in an abdominal cavity. FIG. 12 is a view for explaining procedures for fixing a camera to be installed in an abdominal cavity to an abdominal wall by illustrating a state in which a hook needle, which hooks a wire of the camera to be installed in an abdominal cavity, is pulled up. FIG. 13 is a view for explaining procedures for fixing a camera to be installed in an abdominal cavity to an abdominal wall by illustrating a state in which a hook needle is pulled up and a fixing unit is lowered along the hook needle. FIG. 14 is a sectional view for explaining an action of an extracorporeal device. FIG. 15 is a view illustrating a state in which a fixing unit is installed on an abdomen and a camera to be installed in an abdominal cavity is fixed to an abdominal wall. FIG. 16 is a sectional view of the fixing unit and the camera to be installed in an abdominal cavity in the state shown in FIG. 15. FIG. 17 is an entire configuration diagram of an endoscope system illustrating a state in which a camera to be installed in an abdominal cavity is fixed to an abdominal wall. FIG. 18 is a sectional view for explaining procedures for removing a fixing unit from a wire of a camera to be installed in an abdominal cavity. FIG. 19 is a view for explaining procedures for changing a position of a camera to be installed in an abdominal cavity by illustrating a state in which another position of an abdominal wall is punctured with a hook needle to hook a wire of the camera to be installed in an abdominal cavity. FIG. 20 is a view illustrating a state in which a fixing unit is installed on an abdomen and a camera to be installed in an abdominal cavity is fixed to an abdominal wall after changing the position.

As shown in FIG. 1, an endoscope system 1 of the present embodiment for performing a laparoscopic surgery is mainly constituted by a rigid endoscope 2 that is a first shooting apparatus, an extracorporeal device 3, a very small camera to be installed in an abdominal cavity (abbreviated to camera below) 4 that is a second shooting apparatus and an image pickup apparatus, a light source device 5, a camera control unit (abbreviated to CCU below) 6 that is a signal processing device in which an image processing circuit is incorporated, and a display device 7 that is connected to the CCU 6 via a communication cable 13 and displays an observation image.

The light source device 5 supplies an illuminating light to an illuminating optical system provided in the rigid endoscope 2. The light source device 5 and the rigid endoscope 2 are removably connected by a light source cable 10.

The rigid endoscope 2 is mainly constituted by a rigid insertion portion 8, and an operation portion 9 sequentially connected to a proximal end of the insertion portion 8. In the insertion portion 8 of the rigid endoscope 2, an image guide and a light guide bundle are inserted through its interior portion, and a shooting optical system for focusing a subject image onto a rigid endoscope camera described below via the image guide, and the illuminating optical system for emitting an illuminating light from the light guide bundle toward a subject are disposed on its distal end surface.

An unillustrated camera head in which a solid-state image pickup device such as CCD and CMOS is disposed is incorporated in the operation portion 9 of the rigid endoscope 2. An optical image of an observed region illuminated by the illuminating light supplied from the light source device 5 to the rigid endoscope 2 through the light source cable 10 is picked up by the camera head in the operation portion 9 through the image guide in the insertion portion 8. The rigid endoscope camera photoelectrically converts the picked-up optical image into an image pickup signal, which is transmitted to the CCU 6 through an image pickup cable 11. In the rigid endoscope 2 of the present embodiment, an image pickup optical system is set such that its angle of view α in which images can be shot (see FIG. 17) is 70° to 75°, for example.

The CCU 6 generates a video signal from the transmitted image signal, and outputs the video signal to the display device 7. The display device 7 is a liquid crystal display, for example. The display device 7 receives the video signal outputted from the CCU 6, and displays both a normal observation image by the rigid endoscope 2 and a wide-angle observation image by the camera 4 on one screen or switches the normal observation image and the wide-angle observation image to separately display the images on the screen. Also, the CCU 6 is removably connected to a fixing unit 15 of the extracorporeal device 3 described below via an electric cable 12.

Next, the extracorporeal device 3 will be described in detail below with reference to FIGS. 2 and 3.

The extracorporeal device 3 includes the fixing unit 15 for pulling and fixing the camera 4 in a body cavity, and a hook needle 16 that is a puncture needle for hooking and pulling up the camera 4 as shown in FIGS. 2 and 3.

The fixing unit 15 has a receiver 22 and an electrical connector portion 23 electrically connected to the receiver 22, which are incorporated in a housing 21 formed of a nonmagnetic material. The electrical connector portion 23 is connected to the electric cable 12 that is connected to the CCU 6. Through the electric cable 12, the fixing unit 15 receives power from the CCU 6 and transmits a signal from the receiver 22 to the CCU 6.

A slide hole portion 24 is formed in the housing 21 from a side surface in a lateral direction. A wire fixing lever 26, which constitutes a fixing portion formed of a nonmagnetic material, where an urging spring 25 is fixed to its end surface, is inserted and disposed in the slide hole portion 24. The wire fixing lever 26 has a substantially rectangular parallelepiped shape, and is slidably disposed along the slide hole portion 24 in an inward direction of the housing 21. Also, a hole portion 27 having a convex-shaped arc surface 27a on the urging spring 25 side is formed in an intermediate portion of the wire fixing lever 26.

A vertically penetrating wire insertion portion 28 is formed in the housing 21. In the wire insertion portion 28, a cone-shaped tapered surface 29 is formed so as to widen toward a top portion to be an opening on a top surface of the housing 21.

In the fixing unit 15 having the configuration described above, the hook needle 16 is removably inserted and disposed in the vertically penetrating hole with the wire fixing lever 26 being pushed into a slide position in the housing 21 where the hole portion 27 of the wire fixing lever 26 and the wire insertion portion 28 correspond to each other.

The hook needle 16 of the extracorporeal device 3 includes a cylindrical puncture needle tube 31, a needle head 32 sequentially provided in a top portion of the puncture needle tube 31, a puncture rod 33 in which a hook portion 34 slidably inserted into the puncture needle tube 31 is formed in a distal end, a hook head 35 sequentially provided in a top portion of the puncture rod 33, and a spring 36 interposed between the hook head 35 and the needle head 32.

The puncture needle tube 31 is an about 3 mm (in diameter) elongated metal tube body whose distal end is formed to have a sharp needle shape cut off at a slant. The needle head 32 has a larger outer diameter than the puncture needle tube 31, and its distal end side is formed to have a cone shape and is integrally formed with the puncture needle tube 31. The needle head 32 is in abutment with the tapered surface 29 formed on the top portion of the housing 21, so that the hook needle 16 is configured not to fall off from the housing 21.

The puncture rod 33 is an elongated metal stick body. The hook head 35 sequentially provided in the top portion is urged in a direction to be separated from the needle head 32 by the spring 36. Accordingly, the hook portion 34 formed in the distal end of the puncture rod 33 is housed in the puncture needle tube 31.

Also, in the hook needle 16, when a user pushes the hook head 35 into the puncture needle tube 31 against an urging force of the spring 36 (arrow F in FIG. 3), the hook portion 34 formed in the distal end projects from the distal end of the puncture needle tube 31.

With the hook needle 16 having the configuration described above being inserted and disposed in the wire insertion portion 28 of the housing 21 and the hole portion 27 of the wire fixing lever 26, the wire fixing lever 26 is inserted and fixed to the housing 21 due to a pressing force in an outward direction of the housing 21 caused by an urging force of the urging spring 25. That is, an outer periphery surface of the puncture needle tube 31 is pressed by the arc surface 27a formed in one side surface of the hole portion 27 of the wire fixing lever 26 and is in abutment with an inner surface of the wire insertion portion 28, so that the hook needle 16 is fixed in a state in which the hook needle 16 is inserted through the housing 21.

The hook needle 16 of the extracorporeal device 3 may be configured as the forceps-type puncture needle shown in FIGS. 4 and 5, or the clip-type puncture needle shown in FIGS. 6 and 7.

In the forceps-type puncture needle shown in FIGS. 4 and 5, an operation wire 33a is inserted through the puncture rod 33, and an opening and closing jaw 37 can be opened and closed around a rotation axis 37a with respect to the puncture rod 33 by a pulling and loosening operation of the operation wire 33a.

Also, saw-tooth concavities and convexities 38 are formed on a side portion of the puncture rod 33, and the opening and closing jaw 37 is engaged with the concavities and convexities 38. By using the forceps-type puncture needle as described above, a wire 45 of the camera 4 described below can be reliably held by the opening and closing jaw 37.

Moreover, in the clip-type puncture needle shown in FIGS. 6 and 7, a claw portion 39 is provided in the hook portion 34 of the puncture rod 33. The claw portion 39 is disposed adjacent to or in contact with a claw receiver 39a on the side of a distal end side portion of the puncture rod 33. The claw portion 39 has an elastic portion 39b that is deformed by a predetermined amount of force.

Since the claw portion 39 is deformed inward of the hook portion 34 with the elastic portion 39b being a support portion, the clip-type puncture needle can hook the wire 45 of the camera 4 such that the wire 45 is difficult to fall off from the hook portion 34.

Next, the camera 4 will be described in detail below with reference to FIG. 8.

The camera 4 is mainly constituted by a camera body 41 and an abdominal wall fixing portion 42 that is a contact portion with a wall within a body, which are sequentially provided, as shown in FIG. 8.

The camera body 41 is a so-called capsule-type image pickup unit. Its outer shape is formed with a substantially dome-shaped transparent hood 51 on a distal end side (on a lower side in FIG. 8), and a camera housing 52 formed of a nonmagnetic material in which the transparent hood 51 is disposed so as to hermetically seal one surface.

In the camera housing 52, a plurality of white LEDs 53, two white LEDs 53 here, as illuminating portions, which are light sources of an illuminating light, are disposed on one surface on the transparent hood 51 side. Also, an objective lens group 54 held in a lens holding hole that is formed in substantially the center of the above surface, and a solid-state image pickup device unit 55 such as CCD and CMOS in which a light receiving portion is disposed in a position where a shooting light is focused by the objective lens group 54 are provided.

Also, in the camera housing 52, a transmitter 57 is disposed, and a battery 56 for feeding power to the transmitter 57, the white LEDs 53 and the solid-state image pickup device unit 55 is incorporated. In a functional section of the camera body 41 in the present embodiment, an image pickup optical system that picks up an image in a wide-angle visual field area is set such that its angle of vision β in which images can be shot (see FIG. 17) is 90° or more, for example. An image signal photoelectrically converted by the solid-state image pickup device unit 55 is wirelessly transmitted from the transmitter 57 to the receiver 22 disposed in the housing 21 of the extracorporeal device 3.

The abdominal wall fixing portion 42 is formed of a flexible elastic member such as silicone rubber, for example. The abdominal wall fixing portion 42 includes a connecting portion 61 fitted into a proximal end portion of the camera housing 52, and a suction cup 62, which is a pressure adjusting portion on the camera 4 side, in a top end portion that is a proximal end side of the connecting portion 61. Also, a convex portion 63 that projects in a cylindrical shape in substantially the center of a surface of the suction cup 62, and a through hole 64 in the center of the connecting portion 61 so as to be in communication with a hole portion of the convex portion 63 are formed in the abdominal wall fixing portion 42.

A hoisting wire 45 having a predetermined length is inserted through the through hole 64 of the abdominal wall fixing portion 42. A coupling portion 65 connected by caulking is provided in one end portion of the wire 45. The coupling portion 65 is fitted and fixed to the center of a proximal end surface of the camera housing 52. That is, the wire 45 is provided so as to extend from the center of the suction cup 62. By pulling the wire 45 with a given tensile force or more, the suction cup 62 formed of an elastic member sticks to a wall within a body with an end portion of the suction cup 62 being widened and deformed. The wire 45 may be a thread such as a surgical suture, or a stranded wire made of metal.

The endoscope system 1 in the present embodiment having the configuration described above is used for a laparoscopic surgery, and is used for a treatment in an abdominal cavity that is one of body cavities of a patient.

Here, procedures for installing the endoscope system 1 of the present embodiment in an abdominal cavity as a body cavity of a patient for the laparoscopic surgery, and its action will be described in detail below with reference to FIGS. 9 to 20.

First, an operator makes two small dissections in an abdominal wall 102 of a patient 100 by using a surgical knife or the like, and punctures the dissections with trocars 110 and 111 as shown in FIG. 9. Here, the operator makes a puncture into an abdominal cavity 101 with the trocar 111 for introducing a treatment instrument 120 such as a grasping forceps into the abdominal cavity 101 by dissecting the abdominal wall 102 or the like in another position apart a predetermined distance from the trocar 110 for introducing the rigid endoscope 2 into the abdominal cavity 101.

Also, the operator inserts the puncture needle tube 31 of the hook needle 16 into the wire insertion portion 28 provided in the fixing unit 15 of the extracorporeal device 3 as shown in FIG. 10. At this time, the operator pushes the wire fixing lever 26 into the housing 21 such that the puncture needle tube 31 penetrates the fixing unit 15, and inserts the puncture needle tube 31 such that the puncture needle tube 31 penetrates the hole portion 27 of the wire fixing lever 26.

The operator allows the puncture needle tube 31 to sufficiently project from a bottom surface of the fixing unit 15 such that the fixing unit 15 is sufficiently located on the needle head 32 side that is a hand side of the puncture needle tube 31 (see FIGS. 2 and 3). In this state, the arc surface 27a that is one wall surface of the hole portion 27 of the wire fixing lever 26 is in abutment with and holds the puncture needle tube 31 by the urging force of the urging spring 25 on the wire fixing lever 26, so that the fixing unit 15 does not fall off from the puncture needle tube 31.

Next, as shown in FIG. 10, the operator inserts the insertion portion 8 of the rigid endoscope 2 into the abdominal cavity 101 through the trocar 110. The operator inserts the camera 4 grasped by the treatment instrument 120 such as a grasping forceps into the abdominal cavity 101 through the trocar 111. At this time, the operator may insert the camera 4 into the abdominal cavity 101 while checking an image by the rigid endoscope 2.

Also, when the camera 4 is introduced into the abdominal cavity 101 through the trocar 111, the convex portion 63 (see FIG. 8) that projects in a cylindrical shape in substantially the center of the surface of the suction cup 62 is grasped by the treatment instrument such as a grasping forceps. Since the convex portion 63 is provided in substantially the center of the surface of the suction cup 62, the camera 4 can be easily grasped by the treatment instrument in a balanced manner. Accordingly, the operator can easily insert the camera 4 into the trocar 111 at the time of introducing the camera 4 into the abdominal cavity, that is, can easily introduce the camera 4 into the abdominal cavity 101 such that the camera 4 is not caught in the trocar 111.

Next, the operator punctures the abdominal wall 102 with the puncture needle tube 31 of the hook needle 16 which is being inserted and held in the fixing unit 15 that constitutes the extracorporeal device 3 such that the puncture needle tube 31 penetrates the abdominal wall 102 while checking the image by the rigid endoscope 2 as shown in FIGS. 10 and 11. In order to guide the puncture rod 33 from the puncture needle tube 31 as shown in FIG. 11, the operator pushes the hook head 35 in a direction indicated by an arrow F in FIG. 11. From the state, the operator hooks the wire 45 of the camera 4 into the hook portion 34 formed in the puncture rod 33 while watching the image by the rigid endoscope 2.

When the wire 45 is hooked into the hook portion 34, the operator releases the pushing of the hook head 35 of the puncture rod 33. The puncture rod 33 is thereby introduced into the puncture needle tube 31 with the wire 45 being hooked into the hook portion 34.

After that, the operator extracts the puncture needle tube 31 of the hook needle 16 from the abdominal cavity 101 to outside a body (UP direction in FIG. 12) with the wire 45 being hooked into the hook portion 34 of the puncture rod 33 as shown in FIG. 12. The operator moves the fixing unit 15 relative to the puncture needle tube 31 in an abdomen direction of the patient 100 (DOWN direction in FIG. 13) while extracting the puncture needle tube 31 of the hook needle 16 from the abdominal cavity 101, and pulls the puncture needle tube 31 until the wire 45 passes through the wire insertion portion 28 of the fixing unit 15 as shown in FIG. 13.

At this time, by pushing the wire fixing lever 26 of the fixing unit 15 into the housing 21 (arrow P direction in FIG. 14), the operator can easily slide the fixing unit 15 relative to the puncture needle tube 31 of the hook needle 16. When the wire 45 passes through the wire insertion portion 28 of the fixing unit 15, the operator moves the fixing unit 15 relative to the wire 45 in the abdomen direction of the patient 100 (DOWN direction in FIG. 14) while pulling the wire 45 itself (UP direction in FIG. 14) as shown in FIG. 14.

That is, the operator can easily slide the fixing unit 15 relative to the puncture needle tube 31 of the hook needle 16 and the wire 45 of the camera 4 by maintaining a state in which the wire fixing lever 26 of the fixing unit 15 is pushed into the housing 21.

Then, as shown in FIG. 15, the operator pulls the wire 45 of the camera 4 until the abdominal wall 102 is sandwiched between the fixing unit 15 and the camera 4 in a state in which the fixing unit 15 is placed on the abdomen of the patient 100. At this time, the operator releases the pushing of the wire fixing lever 26 of the fixing unit 15 when confirming that the suction cup 62 of the camera 4 sticks to an inner surface of the abdominal wall 102 as shown in FIG. 16 from the image by the rigid endoscope 2.

The wire fixing lever 26 of the fixing unit 15 is thereby moved in a direction of an arrow R in FIG. 16 upon reception of the urging force of the urging spring 25, so that the hole portion 27 is misaligned with the wire insertion portion 28 of the housing 21. The wire 45 inserted through the hole portion 27 and the wire insertion portion 28 is caught therein and is thereby fixed to the housing 21. At this time, due to the deformation of the suction cup 62 having elasticity, a given tensile force or more is always applied to the wire 45 between the fixing lever 26 and the suction cup 62. Accordingly, the given tensile force or more applied to the wire 45 at all times is maintained, so that the fixing unit 15 and the camera 4 are fixed with the abdominal wall 102 being sandwiched therebetween.

As shown in FIG. 17, the camera 4 is thereby installed in a reliably stable state in the abdominal cavity 101 of the patient 100, and the laparoscopic surgery is performed by the endoscope system 1 of the present embodiment. One end portion of an unillustrated insufflation tube is attached to the trocar 110, for example, and a carbon dioxide gas or the like is injected into the abdominal cavity as an insufflation gas for the purpose of securing a visual field of the rigid endoscope 2 and a region in which an operation instrument or the like is operated, for example. The operator inserts the rigid endoscope 2 through the trocar 110 and the treatment instrument 120 through the trocar 111 to perform the laparoscopic surgery in a state in which the camera 4 sticks to the abdominal wall 102 to be placed in the abdominal cavity 101.

Also, when the operator wants to change a fixed position of the camera 4 in the abdominal cavity 101 of the patient 100, the operator removes the fixing unit 15 from the wire 45 while pushing the wire fixing lever 26 of the fixing unit 15 into the housing 21 in a state in which the camera 4 is grasped by the treatment instrument 120 in the abdominal cavity 101 as shown in FIG. 18. After that, the operator inserts and disposes the hook needle 16 in the wire insertion portion 28 of the fixing unit 15 as described above.

Then, the operator makes a small dissection in the abdominal wall 102 of the patient 100 in a desired position by using a surgical knife or the like, and reinserts the trocar 110 into the dissection. Subsequently, the operator introduces the rigid endoscope 2 into the abdominal cavity 101 through the reinserted trocar 110 as shown in FIG. 19. The operator makes a puncture with the puncture needle tube 31 of the hook needle 16 inserted and disposed in the fixing unit 15 from outside the body into the abdominal cavity 101 in a position where the camera 4 is to be installed.

From the above state, the operator pushes the hook head 35 of the hook needle 16 to guide the puncture rod 33 from the puncture needle tube 31 and hook the wire 45 of the camera 4 into the hook portion 34 while checking the image by the rigid endoscope 2. Then, the operator removes the hook needle 16 from the fixing unit 15 as described above, and pulls the wire 45 inserted through the fixing unit 15 to fix the fixing unit 15 and the camera 4 such that the abdominal wall 102 is sandwiched between the fixing unit 15 and the camera 4 (see FIG. 20).

The endoscope system 1 in the present embodiment can easily change a visual field direction of the camera 4 in the abdominal cavity 101 by imposing a burden on the patient as little as possible as described above. That is, it is preferable to perform the laparoscopic surgery by locating the camera 4 in a position where an organ in the abdominal cavity 101 extensively shot by the camera 4 can be easily diagnosed. The operator can easily change the fixed position of the camera 4 in the abdominal cavity 101.

Also, when the laparoscopic surgery is completed, the operator removes the fixing unit 15 from the wire 45 while pushing the wire fixing lever 26 of the fixing unit 15 into the housing 21. The operator grasps the camera 4 in the abdominal cavity 101 by the treatment instrument 120 such as a grasping forceps, and removes the camera 4 from the abdominal cavity 101 to outside the body through the trocar 111.

According to the endoscope system 1 of the present embodiment described above, body tissue in a body cavity, the abdominal cavity 101 here, can be observed from a plurality of viewpoints including a wide angle. Thus, an operation of a large organ can be performed, or an entire resection line at the time of resecting a large intestine can be easily recognized, for example. Also, when the camera 4 to be introduced into the abdominal cavity 101 separately from the rigid endoscope 2 for magnification observation is installed, a minimally invasive surgical operation can be performed using the endoscope system 1 without increasing a burden on the patient. As a result, the treatment by the laparoscopic surgery becomes easy by using the endoscope system 1 of the present invention.

(Second Embodiment)

Figure 21:
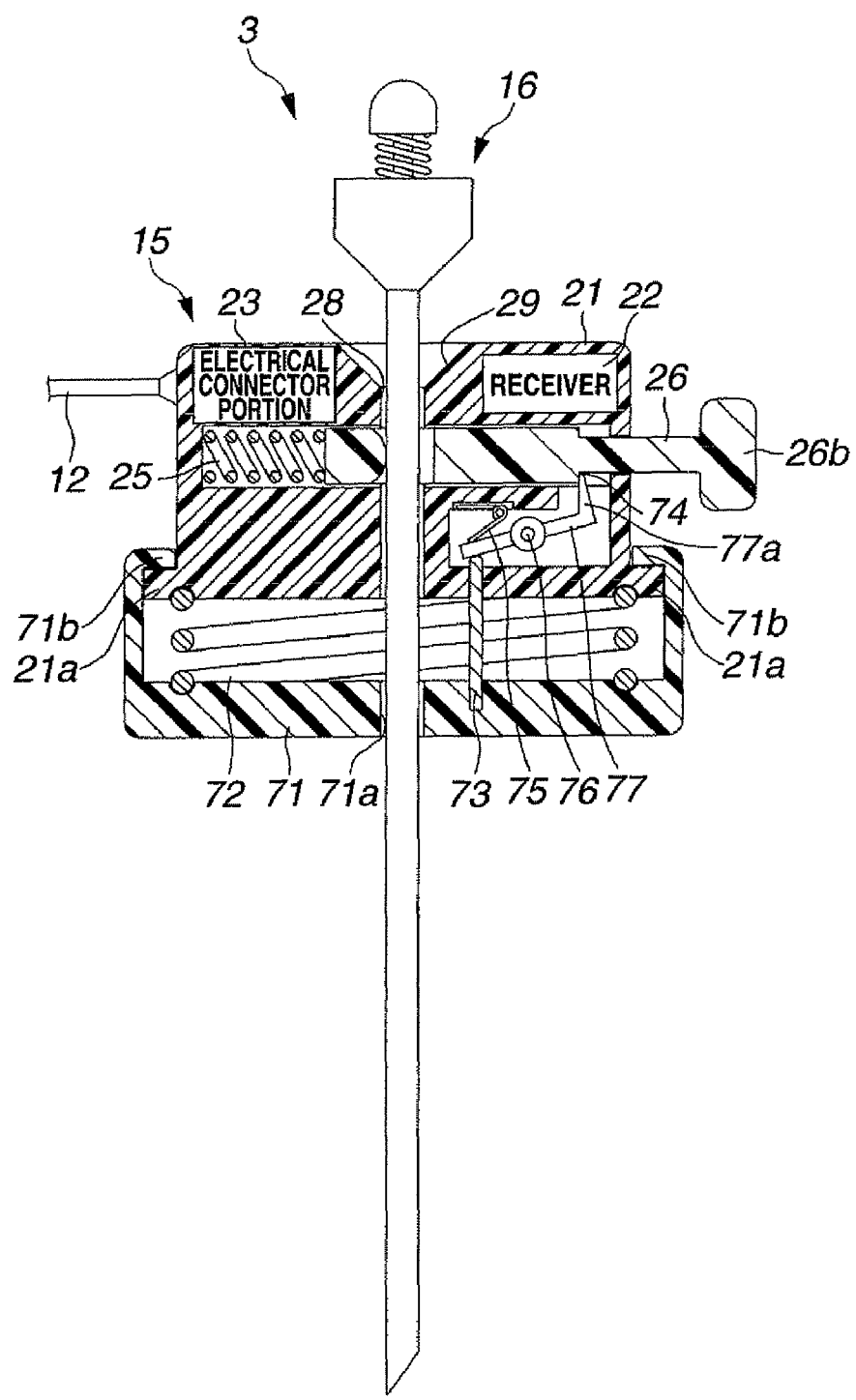
FIG. 21 is a sectional view of an extracorporeal device according to a second embodiment of the present invention.
Figure 22:
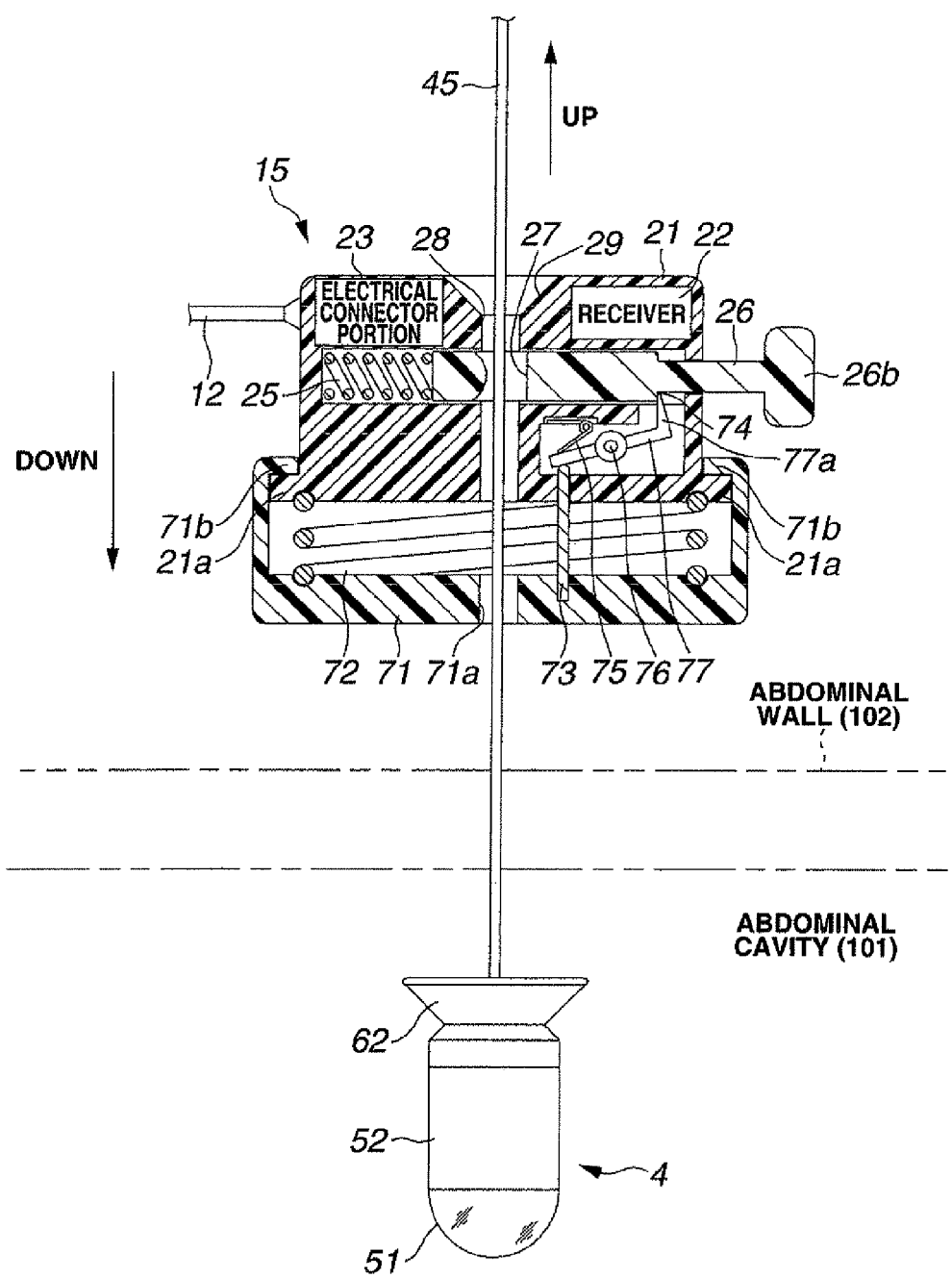
FIG. 22 is a sectional view of a fixing unit and a camera to be installed in an abdominal cavity for explaining procedures for fixing the fixing unit and the camera to be installed in an abdominal cavity to an abdominal wall according to the second embodiment.
Figure 23:
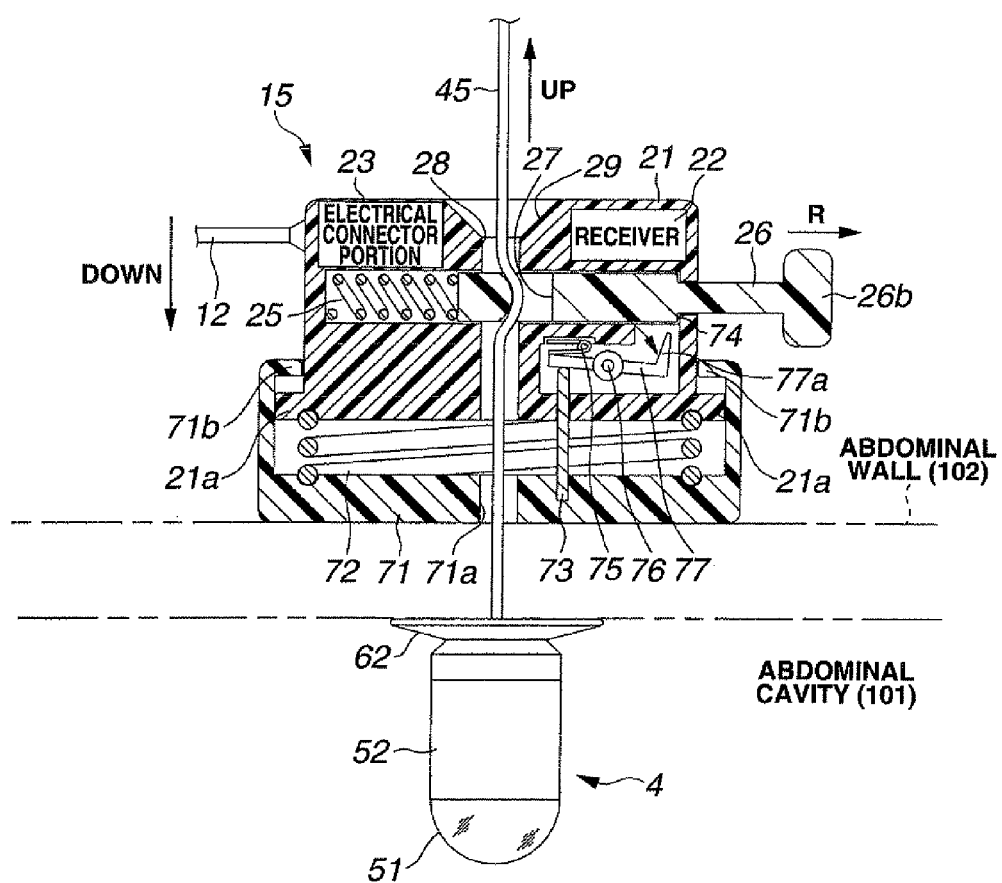
FIG. 23 is a sectional view of a fixing unit and a camera to be installed in an abdominal cavity being fixed to an abdominal wall according to the second embodiment.
Figure 24:
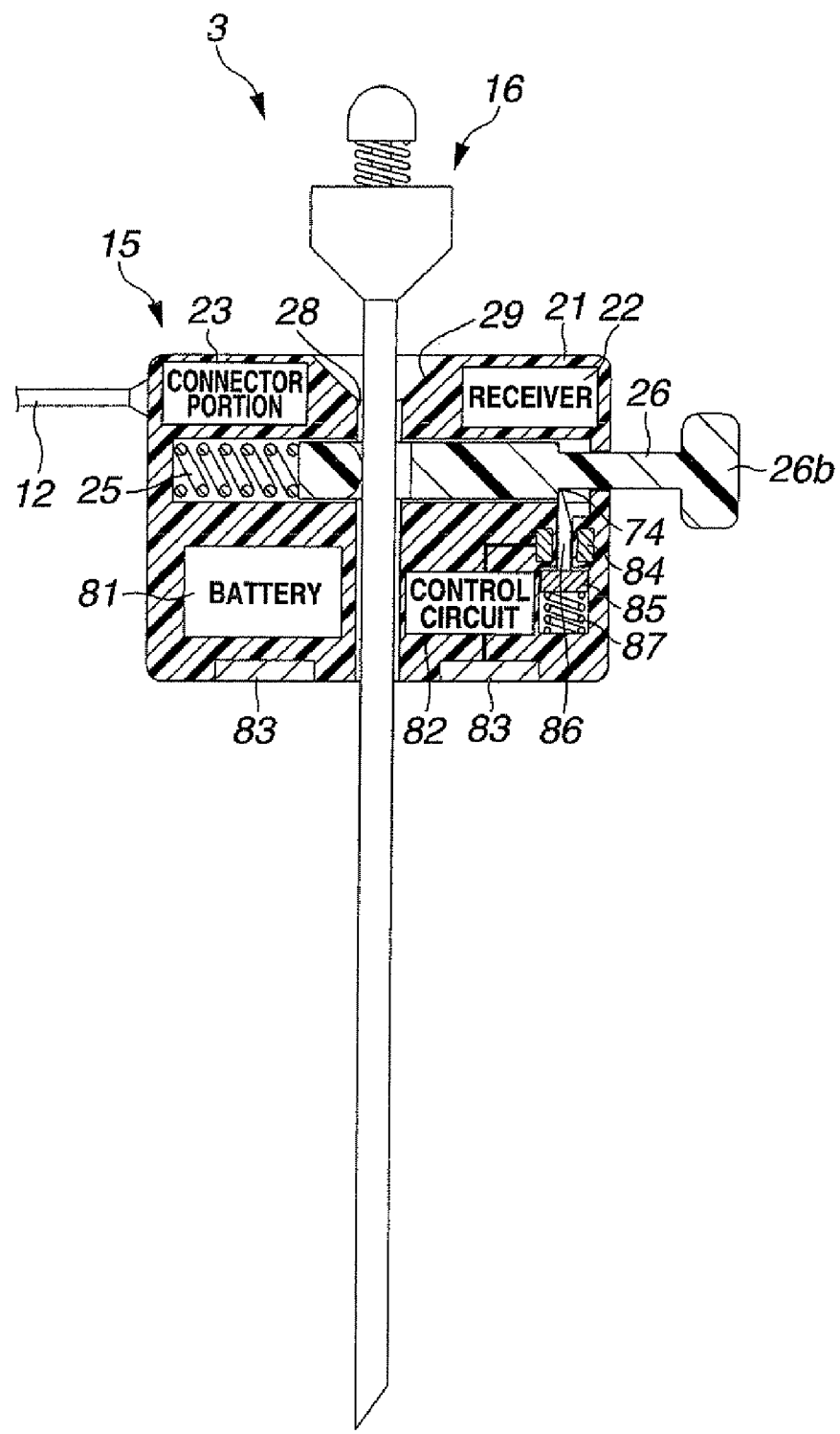
FIG. 24 is a sectional view of an extracorporeal device illustrating a modification according to the second embodiment.

Next, a second embodiment according to the endoscope system of the present invention will be described below with reference to FIGS. 21 to 24. FIGS. 21 to 24 are related to the second embodiment of the present invention. FIG. 21 is a sectional view of an extracorporeal device. FIG. 22 is a sectional view of a fixing unit and a camera to be installed in an abdominal cavity for explaining procedures for fixing the fixing unit and the camera to be installed in an abdominal cavity to an abdominal wall. FIG. 23 is a sectional view of a fixing unit and a camera to be installed in an abdominal cavity being fixed to an abdominal wall. FIG. 24 is a sectional view of an extracorporeal device illustrating a modification. In the following description, the same constituent elements as those in the endoscope system 1 of the first embodiment described above are assigned the same reference numerals to omit the detailed description thereof.

The fixing unit 15 of the extracorporeal device 3 in the present embodiment includes a pressure detecting mechanism as a pressure adjusting portion on the extracorporeal device 3 side, in which the wire fixing lever 26 is moved to fix the wire 45 to the housing 21 when a predetermined pressure is applied to the housing 21 which is pressed by the abdominal wall 102.

To be more specific, a lock body 77 including a claw portion 77a hooked on a step portion 74 of the wire fixing lever 26 at one end is rotatably disposed by a rotation axis 76 in the housing 21 of the extracorporeal device 3. In the lock body 77, one end is urged downward by a torsion spring 75 along the rotation axis 76 such that the claw portion 77a on the other end side is moved upward.

A hollow skirt body 71 is disposed so as to be slidable in a vertical direction in a bottom portion of the housing 21. In the skirt body 71, an inward-directed flange 71b is formed in an opening of a top portion, and a hole portion 71a through which the hook needle 16 and the wire 45 are inserted is provided in a bottom portion. Also, the inward-directed flange 71b is in abutment with an outward-directed flange 21a formed in a bottom side portion of the housing 21, so that the skirt body 71 is disposed so as not to fall off from the housing 21.

A spring 72 is provided inside the skirt body 71. The spring 72 urges the housing 21 and the skirt body 71 such that the housing 21 and the skirt body 71 are separated from each other in a vertical direction. Also, a pin 73, which projects from a bottom surface of an interior portion to penetrate into the housing 21 and pushes up the lock body 77 upward along the rotation axis 76 against an urging force of the torsion spring 75, is disposed in the skirt body 71.

That is, the fixing unit 15 has a configuration in which the pin 73 pushes up the lock body 77 upward along the rotation axis 76 when the skirt body 71 is moved upward and the housing 21 is moved downward against an urging force of the spring 72.

In the wire fixing lever 26 of the present embodiment, an operation button portion 26b is integrally formed in an end portion that projects outside the housing 21.

In the extracorporeal device 3 of the present embodiment having the configuration described above, at the time of installing the camera 4 and the fixing unit 15 in a patient, the wire 45 is pulled out to outside of a body by the hook needle 16 and the pulled out wire 45 is allowed to pass through the wire insertion portion 28 and the hole portion 71a of the fixing unit 15 as shown in FIG. 22 in a similar manner to the first embodiment. Subsequently, the wire 45 is pulled (UP direction in FIG. 22), so that the fixing unit 15 of the extracorporeal device 3 is moved in an abdomen direction (DOWN direction in FIG. 22) of the patient 100.

Then, with the fixing unit 15 being placed on the abdomen of the patient 100, the wire 45 of the camera 4 is pulled until the abdominal wall 102 is sandwiched between the fixing unit 15 and the camera 4. At this time, as shown in FIG. 23, when the housing 21 of the fixing unit 15 is pressed into the skirt body 71 with a predetermined pressure or more (DOWN direction in FIG. 23), or when the skirt body 71 is moved into the housing 21 side (UP direction in FIG. 23), the pin 73 pushes up the lock body 77 upward along the rotation axis 76 against the urging force of the torsion spring 75.

The claw portion 77a is thereby unhooked from the step portion 74, so that the wire fixing lever 26 of the fixing unit 15 receives the urging force of the urging spring 25 to be moved in a direction of an arrow R in FIG. 23. The hole portion 27 is thereby misaligned with the wire insertion portion 28 of the housing 21. Accordingly, the wire 45 inserted through the hole portion 27 and the wire insertion portion 28 is caught by the wire fixing lever 26 and is fixed to the housing 21. The fixing unit 15 and the camera 4 are thereby fixed with the abdominal wall 102 being sandwiched therebetween.

From the above, the fixing unit 15 in the present embodiment has a configuration in which the wire fixing lever 26 is moved and the wire 45 is fixed when a predetermine pressure or more is applied in a direction where the housing 21 and the skirt body 71 approach each other against the spring 72 with the abdominal wall 102 being sandwiched between the fixing unit 15 and the camera 4.

Also, the skirt body 71 on the abdominal wall 102 receives a force in a direction to be separated from the housing 21 by the spring 72. A force in a direction to be separated from the abdominal wall 102 also acts on the suction cup 62 of the camera 4 due to its elastic force. Accordingly, a force in a direction where the housing 21 that fixes the wire 45 and the camera 4 are separated from each other is applied at all times, so that the fixing unit 15 and the camera 4 are reliably fixed with the abdominal wall 102 being sandwiched therebetween by maintaining a given tensile force or more at all times by a contact surface of the skirt body 71 and a suction surface of the suction cup 62 of the camera 4, which hold the abdominal wall 102.

As described above, the endoscope system 1 of the present embodiment has a configuration in which the hook needle 16 and the wire 45 are easily inserted and removed and operability is improved since the lock body 77 is hooked when an operator pushes the wire fixing lever 26 of the fixing unit 15 into the housing 21 once and the state in which the wire fixing lever 26 is pushed into the housing 21 is maintained, in addition to the effects in the first embodiment.

The pressure detecting mechanism as the pressure adjusting portion on the extracorporeal device 3 side may have a configuration in which the fixation of the wire fixing lever 26 is electrically released by a pressure sensor 83 as shown in FIG. 24.

To describe in detail, in the housing 21 of the fixing unit 15, a battery 81, a control circuit 82, the pressure sensor 83, a vertically slidable claw portion 86 having a solenoid mechanism by an electromagnet 84 and a permanent magnet 85, and a spring 87 for urging the permanent magnet 85 upward with the claw portion 86 are provided. A magnetic force generated by the electromagnet 84 and a magnetic force of the permanent magnet 85 toward the electromagnet 84 side are set to have the same pole. That is, the electromagnet 84 and the permanent magnet 85 are set to repel each other.

The pressure sensor 83 is disposed on a bottom surface portion of the housing 21, and is electrically connected to the control circuit 82. The battery 81 supplies driving power to the control circuit 82 and the pressure sensor 83.

The control circuit 82 is electrically connected to the electromagnet 84, and feeds power and stops feeding power to turn ON/OFF the electromagnet 84 based on a detection signal of the pressure sensor 83. Also, a predetermined contact pressure is set in the pressure sensor 83. When detecting a pressure larger than the predetermined contact pressure, the pressure sensor 83 outputs the detection signal to the control circuit 82.

When the detection signal from the pressure sensor 83 is not inputted, the control circuit 82 stops feeding power to the electromagnet 84. At this time, the permanent magnet 85 is moved upward with the claw portion 86 by an urging force of the spring 87.

The claw portion 86 receiving the force moving upward is hooked on the step portion 74 of the wire fixing lever 26 when the wire fixing lever 26 is pushed into the housing 21. Accordingly, the state in which the wire fixing lever 26 is pushed into the housing 21 is maintained.

In the extracorporeal device 3 having the configuration described above, at the time of installing the camera 4 and the fixing unit 15 in a patient, the wire 45 is pulled out to outside of a body by the hook needle 16, and the pulled out wire 45 is allowed to pass through the wire insertion portion 28 and the hole portion 71*a* of the fixing unit 15 in a similar manner to the above description. Subsequently, with the fixing unit 15 being placed on the abdomen of the patient 100, the wire 45 of the camera 4 is pulled until the abdominal wall 102 is sandwiched between the fixing unit 15 and the camera 4.

When the detection signal obtained when the pressure sensor 83 detects a predetermined pressure on an abdomen body surface of the patient 100 is inputted, the control circuit 82 feeds power to the electromagnet 84. The permanent magnet 85 thereby repels the electromagnet 84, and is moved downward with the claw portion 86 against the urging force of the spring 87.

The claw portion 86 is thereby unhooked from the step portion 74 of the wire fixing lever 26, and the wire fixing lever 26 is moved in an outward direction from the housing 21 upon reception of the urging force of the urging spring 25. That is, the hole portion 27 of the wire fixing lever 26 is misaligned with the wire insertion portion 28 of the housing 21. Accordingly, the wire 45 inserted through the hole portion 27 and the wire insertion portion 28 is caught by the wire fixing lever 26, and is fixed to the housing 21. The fixing unit 15 and the camera 4 are thereby fixed with the abdominal wall 102 being sandwiched therebetween by maintaining a given tensile force or more at all times.

The extracorporeal device 3 described above also produces the same effects as those of the configuration described above with reference to FIGS. 21 to 23.

The invention described in each of the above embodiments is not limited to the embodiments and modifications, and may be effected by making various modifications without departing from the scope in an implementation phase. Furthermore, the aforementioned embodiments include various stages of invention, and various inventions may be extracted by appropriately combining a plurality of constituent features disclosed.

For example, even if some of the constituent features are deleted from all the constituent features disclosed in the embodiments, the configuration obtained by deleting the constituent features may be extracted as the invention so long as the problems to be solved by the invention can be solved and the effects described above can be obtained.

The above described endoscope system 1 that is a medical device includes features in Appendix described below.

From the above description, according to the present invention, a medical device including a medical instrument that can be fixedly installed within a body, capable of performing a minimally invasive surgical operation without increasing a burden on a patient, can be achieved. Furthermore, a medical device capable of stably maintaining a fixed state of a medical instrument such that the medical instrument does not wobble and shake throughout an operation can be achieved.

(Appendix 1)

A medical device including:

a medical instrument introduced into a body cavity and having a suction cup portion that is fixed to a wall within a body, and a wire extending from a center of a suction surface of the suction cup;

an extracorporeal device installed on a body surface and having a puncture needle from and into which a hook portion for hooking the wire projects and retracts, and a hole portion through which the puncture needle can be inserted and removed; and a fixing portion provided in a housing of the extracorporeal device and fixing the wire that is inserted through the hole portion for maintaining a suction state of the suction cup portion to the wall within a body by maintaining a state in which a body wall is sandwiched between the medical instrument and the housing.

(Appendix 2)

The medical device according to Appendix 1, wherein the housing includes a pressure detecting mechanism having a lock body for allowing the fixing portion to maintain a non-fixed state of the wire, and releasing the lock body to fix the wire inserted through the hole portion by the fixing portion when the body wall is sandwiched with a predetermined pressure or more.

(Appendix 3)

The medical device according to Appendix 2, wherein the pressure detecting mechanism detects the predetermined pressure by a pressure sensor disposed in the housing.

(Appendix 4)

A process of installing the medical device according to Appendix 1 in a patient, including:

introducing the medical instrument into the abdominal cavity through a trocar by use of a treatment instrument;

puncturing a predetermined position of an abdomen with the puncture needle from a body surface into the abdominal cavity;

pulling the hook portion up to the body surface side of the abdomen with the wire connected to the medical instrument being hooked into the hook portion;

removing the puncture needle from the extracorporeal device such that the wire is inserted through the extracorporeal device;

placing the housing on the abdomen body surface along the wire while pulling the wire with a predetermined tensile force or more until the body wall is sandwiched between the medical instrument and the housing and the suction cup portion sticks to the wall within a body; and fixing the wire to the housing by the fixing portion.

(Appendix 5)

A process of changing a position of the medical instrument of the medical device installed by the process according to Appendix 4, including:

releasing the fixing portion and moving the housing in a direction to be separated from the abdomen body surface along the wire of the medical instrument;

grasping the medical instrument by use of a treatment instrument introduced into the abdominal cavity through a trocar;

removing the wire from the hole portion of the housing;

inserting the puncture needle into the hole portion of the housing;

puncturing a position different from the predetermined position of the abdomen with the puncture needle from the body surface into the abdominal cavity;

pulling the hook portion up to the body surface side of the abdomen with the wire connected to the medical instrument being hooked into the hook portion;

removing the puncture needle from the extracorporeal device such that the wire is inserted through the extracorporeal device;

placing the housing on the abdomen body surface along the wire while pulling the wire until the body wall is sandwiched between the medical instrument and the housing and the suction cup portion sticks to the wall within a body; and fixing the wire to the housing by the fixing portion.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical device for observing inside of an abdominal cavity, the medical device comprising:
    a camera to be installed in an abdominal cavity capable of being introduced into a body cavity and having a contact portion that is fixed in contact with a wall within a body, an image pickup unit that picks up an image in the abdominal cavity, and a wire capable of being drawn toward the wall within the body;
    an extracorporeal device capable of being installed on a body surface outside of the body and having a hole portion through which the wire can be inserted and removed, a fixing mechanism for fixing the wire inserted through the hole portion, and a housing that is fixable in contact with the body surface; and
    a pressure detecting mechanism provided to the extracorporeal device, the pressure detecting mechanism capable of being installed on the body surface outside of the body, to detect a pressure equal to or larger than a predetermined pressure applied to the housing in contact with the body surface, and drive the fixing mechanism so that the wire is fixed in a state where a predetermined tensile force is maintained, when the camera to be installed in an abdominal cavity is pulled by the wire so that the wall within a body contacts the contact portion, to be drawn toward the wall within a body and installed in a state where the body wall is sandwiched between the contact portion of the camera to be installed in an abdominal cavity and the extracorporeal device.

2. The medical device for observing inside of an abdominal cavity according to claim 1, wherein the extracorporeal device comprises a puncture needle having a holding portion for holding the wire, and the hole portion through which the wire and the puncture needle can be inserted and removed.

3. The medical device for observing inside of an abdominal cavity according to claim 2, wherein the holding portion comprises a hook portion for hooking the wire by projecting and retracting.

4. The medical device for observing inside of an abdominal cavity according to claim 3, wherein the contact portion is an elastic member provided in the medical instrument.

5. The medical device for observing inside of an abdominal cavity according to claim 2, wherein the contact portion is an elastic member provided in the medical instrument.

6. The medical device for observing inside of an abdominal cavity according to claim 1, wherein the contact portion is an elastic member provided in the medical instrument.

7. The medical device for observing inside of an abdominal cavity according to claim 1, wherein:
    the contact portion has a suction cup portion that is capable of being fixed to a wall within a body;
    the wire is extended from a center of a suction surface of the suction cup; and
    a suction state of the suction cup portion to the wall within a body is maintained by the fixing mechanism fixing the wire to maintain a state in which a body wall is sandwiched between the camera to be installed in an abdominal cavity and the housing.

8. The medical device for observing inside of an abdominal cavity according to claim 7, wherein the pressure detecting mechanism disposed in the housing has a lock body that maintains the fixing mechanism when the wire is in a non-fixed state, and releases the lock body to fix the wire inserted through the hole portion by the fixing mechanism when the body wall is sandwiched with a predetermined pressure or more.

9. The medical device for observing inside of an abdominal cavity according to claim 8, wherein the pressure detecting mechanism includes a pressure sensor that detects a pressure applied to the housing.

* * * * *